United States Patent
Chu

(10) Patent No.: US 11,446,473 B2
(45) Date of Patent: Sep. 20, 2022

(54) MEDICAL SYSTEMS, DEVICES, AND RELATED METHODS

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 852 days.

(21) Appl. No.: 16/260,214

(22) Filed: Jan. 29, 2019

(65) Prior Publication Data
US 2019/0232027 A1 Aug. 1, 2019

Related U.S. Application Data

(60) Provisional application No. 62/623,768, filed on Jan. 30, 2018.

(51) Int. Cl.
| | | |
|---|---|---|
| *A61B 1/005* | (2006.01) | |
| *A61B 1/00* | (2006.01) | |
| *A61M 25/09* | (2006.01) | |
| *A61B 18/22* | (2006.01) | |
| *A61M 25/01* | (2006.01) | |

(Continued)

(52) U.S. Cl.
CPC ..... *A61M 25/09041* (2013.01); *A61B 1/0052* (2013.01); *A61B 1/00133* (2013.01); *A61B 18/22* (2013.01); *A61M 25/01* (2013.01); *A61M 25/0113* (2013.01); *A61M 25/09* (2013.01); *A61B 1/0051* (2013.01);
(Continued)

(58) Field of Classification Search
CPC ......... A61M 25/09041; A61M 25/0113; A61B 1/00133; A61B 1/0052; A61B 1/00098
See application file for complete search history.

(56) References Cited

U.S. PATENT DOCUMENTS

| | | | |
|---|---|---|---|
| 5,243,679 A | 9/1993 | Sharrow et al. | |
| 5,730,150 A | 3/1998 | Peppel et al. | |

(Continued)

FOREIGN PATENT DOCUMENTS

| | | |
|---|---|---|
| JP | 2005253652 | 9/2005 |
| JP | 2005319083 | 11/2005 |
| JP | 2005323662 | 11/2005 |

OTHER PUBLICATIONS

International Search Report and Written Opinion issued in International Application No. PCT/US2019/015507, dated May 10, 2019 (16 pages).

*Primary Examiner* — Alexandra L Newton
*Assistant Examiner* — Rynae E Boler
(74) *Attorney, Agent, or Firm* — Bookoff McAndrews, PLLC

(57) ABSTRACT

A medical system includes an insertion device and an insertion device handle. The insertion device handle has a proximal portion and a distal portion, with a delivery shaft extending from the distal portion. The medical system also includes a medical device, including a spool and a medical device handle. The medical device handle has a central opening, and the spool and the medical device handle are rotatably movable to one another and form a channel. The medical system includes an adapter couplable to a portion of the insertion device handle, and the adaptor includes a post element to be received within the central opening of the medical device handle.

19 Claims, 14 Drawing Sheets

(51) Int. Cl.
  *G02B 6/44* (2006.01)
  *A61B 17/00* (2006.01)
(52) U.S. Cl.
  CPC . *A61B 1/00066* (2013.01); *A61B 2017/00477* (2013.01); *G02B 6/4439* (2013.01)

(56) References Cited

U.S. PATENT DOCUMENTS

| | | |
|---|---|---|
| 5,827,202 A | 10/1998 | Miraki et al. |
| 5,843,002 A | 12/1998 | Pecor et al. |
| 7,120,349 B2 | 10/2006 | Elliott |
| 7,485,116 B2 | 2/2009 | Cao |
| 2003/0176880 A1* | 9/2003 | Long ............... A61B 10/04 606/167 |
| 2006/0210230 A1 | 9/2006 | Kline et al. |
| 2009/0118575 A1* | 5/2009 | Ichikawa ........... A61B 1/0051 600/103 |
| 2014/0088497 A1* | 3/2014 | Campbell ........... A61B 1/0052 604/95.04 |
| 2015/0112131 A1* | 4/2015 | Murayama ........... A61B 1/015 600/104 |
| 2017/0215695 A1 | 8/2017 | Harrah et al. |

\* cited by examiner

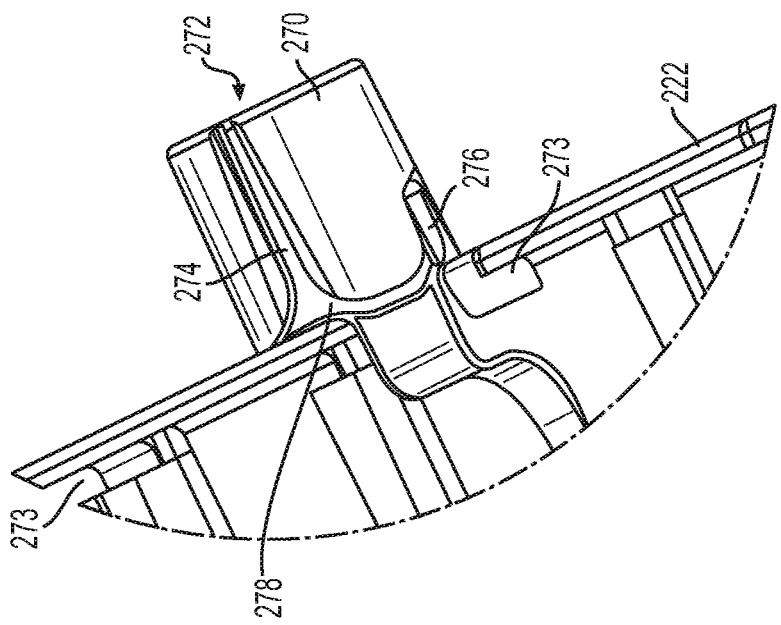
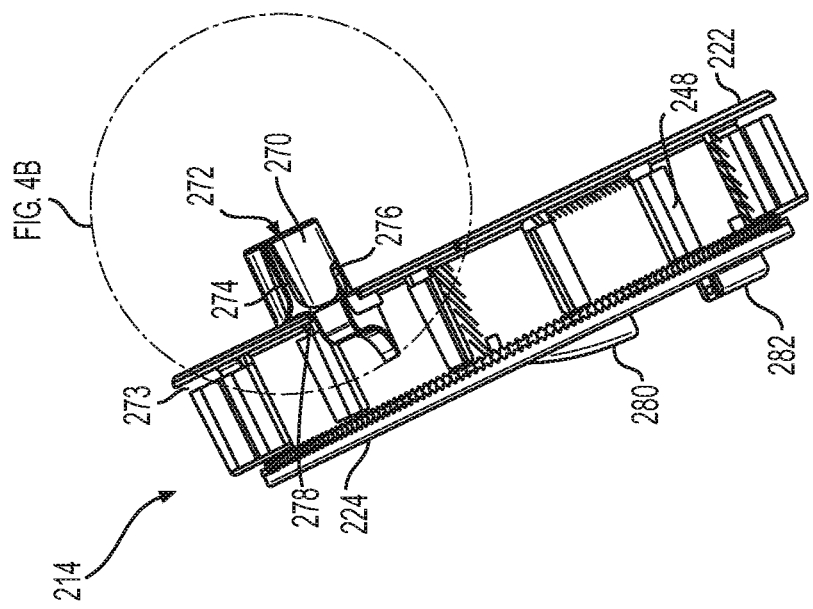

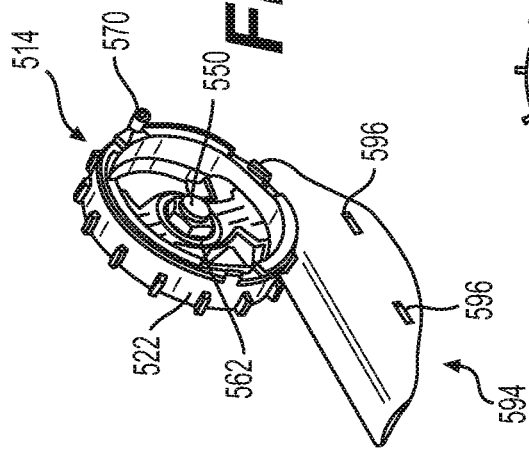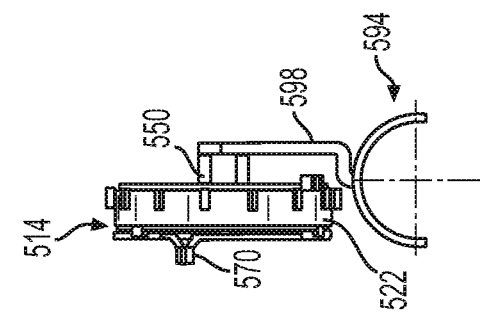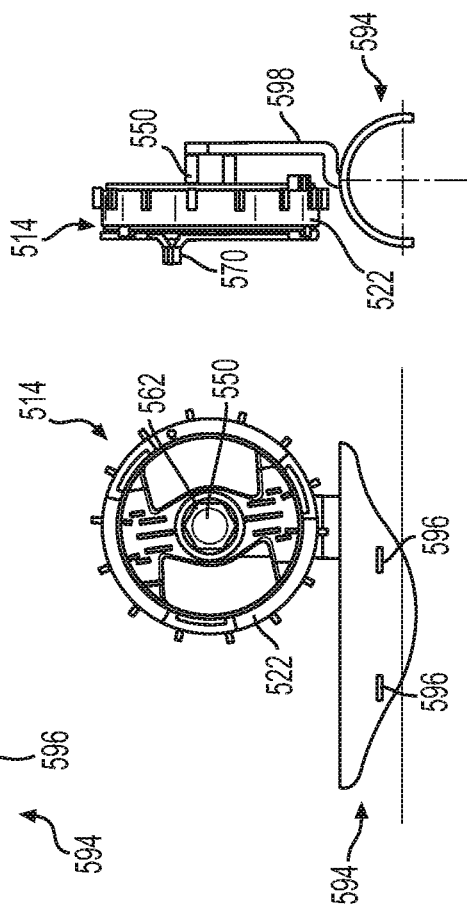

MEDICAL SYSTEMS, DEVICES, AND RELATED METHODS

CROSS-REFERENCE TO RELATED APPLICATIONS

This patent claims the benefit of priority under 35 U.S.C. § 119 to U.S. Provisional Patent Application No. 62/623,768, filed Jan. 30, 2018, which is herein incorporated by reference in its entirety.

TECHNICAL FIELD

Various aspects of the present disclosure relate generally to systems, devices, and methods useful in medical procedures. More specifically, the present disclosure relates to systems, devices, and methods for coupling a medical device to an insertion device to dispense, retract, or otherwise actuate a medical instrument.

BACKGROUND

Guidewires and optical fibers are used in a wide variety of medical procedures, including urology, neurology, otorhinolaryngology, ophthalmology, gastroenterology, cardiology, and gynecology. Generally, a user may control and deliver a guidewire or an optical fiber from packaged spiral loops, but the guidewires and optical fibers may be difficult to handle or easy to damage. For example, a hydrophilic guidewire may be hydrated and made of polyethylene such that the guidewire may be released from a packaged loop, but, as a result, the guidewire may be slippery and difficult to control. Optical fibers are usually packaged such that the entire optical fiber must be removed from the packaging before use, increasing the risk of contamination and breaking between the removal from packaging and the use with a patient. Guidewires and optical fibers also often snag during dispensing or retracting. Moreover, dispensing the guidewire, optical fiber, or other medical device may be cumbersome and difficult to control, especially in the midst of a medical procedure, increasing the chances of user error, further complicating and prolonging the procedure, and exposing the patient to greater risk.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

In one example, a medical system may include an insertion device and an insertion device handle. The insertion device handle may have a proximal portion and a distal portion, with a delivery shaft extending from the distal portion. The medical system may also include a medical device, including a spool and a medical device handle. The medical device handle may have a central opening, and the spool and the medical device handle may be rotatably movable to one another and form a channel. The medical system may also include an adapter couplable to a portion of the insertion device handle, and the adaptor may include a post element to be received within the central opening of the medical device handle.

The medical system may further include one or more of the following features. The medical device may include a coiled element at least partially positioned in the channel between the spool and the medical device handle, and relative rotation of the spool and the medical device handle may extend or retract the coiled element. The coiled element may include an end effector. The coiled element may be at least partially surrounded by a tube or sheath. The spool may include a lock element to secure a proximal end of the coiled element, and the medical device handle may include a guide element to guide the coiled element and the tube or sheath from exterior to within the channel.

The coiled element may be surrounded by a tube, and the tube may include a stop element at a distal end of the tube. The central opening and the post element may be octagonal. The insertion device may include at least one port, and the at least one port may include a seal. A proximal end of the coiled element may extend proximal to the medical device to be coupled to an additional medical device. The insertion device may include a deflection lever positioned on the proximal portion of the insertion device handle on an opposite side of the insertion device handle from the adaptor. The system may be configured for one handed use. The deflection lever may be configured to be operated by a user's thumb, and the medical device may be configured to be operated by a user's forefinger.

The post may include a plurality of projections separated by slots. The spool may include a crank with a throughhole, and the crank may further include a locking slot configured to lock the position of a proximal end of the coiled element. The medical device may further include a control knob movable relative to the spool and including at least one slot. The medical device may further include a plurality of spool teeth positioned on the spool facing the medical device handle, and the medical device handle may include a plurality of handle teeth positioned on the medical device handle facing the spool. The medical system may further include a wave spring between the spool teeth and the handle teeth. The medical system may also further include a second medical device stacked on the adaptor.

In another example, a medical device may include a rotatable spool element including a plurality of spool teeth, a handle element including a plurality of handle teeth, and a biasing member between the spool teeth and the handle teeth. The medical device may also include a rotatable control knob movable relative to the spool element and positioned on the opposite side of the spool element from the biasing member, and a coiled element including a sheath surrounding at least a portion of a drive wire. A distal end of the drive wire may be coupled to an end effector, and the spool element or the handle element may form a channel to house at least a portion of the coiled element.

The medical device may further include one or more of the following features. Rotation of the spool element relative to the handle element may extend or retract the coiled element from the channel. Compression of the medical device in a direction perpendicular to a plane of rotation of the spool member may cause at least a portion of the spool teeth to engage with at least a portion of the handle teeth. When the medical device is compressed, rotation of the control knob relative to the spool element may extend or retract the end effector from within the sheath. The biasing member may be a cantilevered spring.

In a further example, a method of operating a medical system may include inserting an insertion device into a patient, where the insertion device includes a delivery shaft, a deflection mechanism, and at least one port. The method may also include coupling a medical device to the insertion device via an adaptor, and the medical device may include at least a spool, a handle, and a coiled element at least partially stored between or within the spool and the handle. Coupling the medical device via the adaptor may rotatably lock the handle in place. The method may also include delivering the coiled element through the at least one port by rotating the spool.

The method may further include one or more of the following features. The method may further include contemporaneously deflecting a distal end of the delivery shaft by acting on the deflection mechanism and further delivering the coiled element by rotating the spool. The coiled element may include an end effector coupled to a drive wire and a sheath at least partially surrounding the drive. The method may further include extending the end effector distally beyond the sheath by pressing the medical device toward the insertion device and rotating a control knob relative to the spool.

Both the foregoing general description and the following detailed description are exemplary and explanatory only and are not restrictive of the features, as claimed. As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE DRAWINGS

The accompanying drawings, which are incorporated in and constitute a part of this specification, illustrate various exemplary embodiments and together with the description, serve to explain the principles of the disclosure.

FIGS. 4A and 4B illustrate side views of another medical device, according to aspects of the present disclosure.

FIGS. 7A-7C illustrate another medical device and a further medical device adaptor, according to aspects of the present disclosure.

DETAILED DESCRIPTION

Examples of the present disclosure include systems, devices, and methods to facilitate and improve the efficacy, efficiency, and safety of dispensing medical devices during medical procedures. For example, aspects of the present disclosure may provide a user (e.g., a physician, medical technician, or other medical service provider) with the ability to more easily dispense and retract a guidewire, an optical fiber, a retrieval basket, or other shaft-like medical element to be delivered within a patient and/or through an insertion device. Some aspects of the present disclosure may be used in performing an endoscopic, hysteroscopic, or ureteroscopic procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or an insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
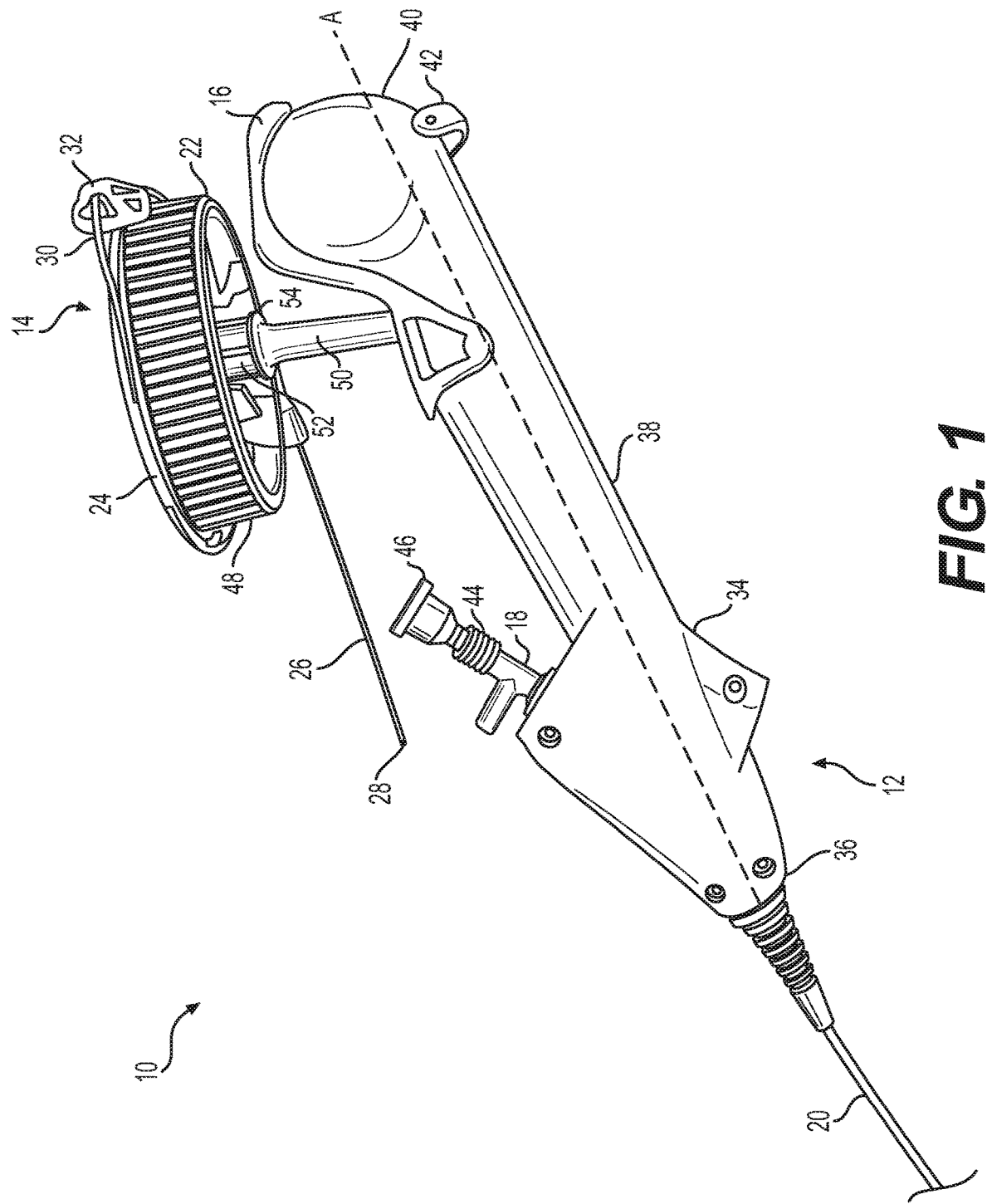
FIG. 1 illustrates a medical system, according to aspects of the present disclosure.

FIG. 1 illustrates a medical system 10 that includes an insertion device 12, a medical device 14, and an adaptor 16. Insertion device 12 may include a port 18 that connects through an internal lumen (not shown) to a delivery shaft 20. Medical device may include a spool 22 and a handle 24, and relative rotation of spool 22 and handle 24 may dispense or retract a coiled element 26 that is at least partially housed within medical device 14. Adaptor 16 may couple medical device 14 to a portion of insertion device 12 such that a user may introduce coiled element 26 through port 18 by action on medical device 14 while also holding insertion device 12. A distal end 28 of coiled element 26 may include an end effector, and a proximal end 30 of coiled element 26 may either be fixedly coupled within medical device 14 or may be extendable proximally to connect to another medical element via proximal connector 32. While much of the below description includes medical device 14 and coiled element 26 being coupled and/or inserted into insertion device 12, the disclosure is not so limited. In alternative embodiments, medical device 14 and coiled element 26 may be detached from insertion device 12, and coiled element 26 may even be detached from medical device 14.

Insertion device 12 may be an ureteroscope (e.g., LithoVue™ Single-Use Digital Flexible Ureteroscope by Boston Scientific Corp.), a hysteroscope, a bronchoscope, a cystoscope, or any similar endoscope device. Insertion device 12 may include a body 34 with a distal portion 36, an intermediate portion 38, and a proximal portion 40. Delivery shaft 20 may extend from distal portion 36 of body 34. Body 34 of insertion device 12 has a longitudinal axis A aligned with a central long axis of a proximal end of the delivery shaft 20. Body 34 may include a deflection lever 42 positioned on a rounded corner of the proximal portion 40.

Deflection lever 42 may be manipulated to deflect a distal end (not shown) of delivery shaft 20. Although not shown, insertion device 12 may include a communication and power conduit connected to a display and power unit. The intermediate portion 38 may have a generally constant diameter, and may form a portion of insertion device 12 that a user may grip such that the user's thumb is proximate deflection lever 42. Proximal portion 40 may be wider than intermediate portion 38.

As mentioned, insertion device 12 includes at least one port 18. The at least one port 18 may include a T-connector as shown in FIG. 1, a Y-connector, or another appropriate connector. Port 18 may include threading 44, may be a female luer, or may include a seal (e.g., a UroLok™ Adaptor seal by Boston Scientific Corp.). The at least one port 18 connects to a proximal end of the delivery shaft 20 through at least one internal lumen (not shown) in the body 34 of insertion device 12. In one aspect, port 18 may include a fitting 46. Fitting 46 may include a seal such that coiled element 26 may be dispensed or retracted through the internal lumen in body 16 and delivery shaft 20 with a reduced likelihood of contamination or backflow of fluids.

As noted above, medical device 14 includes spool 22 and handle 24. Spool 22 and handle 24 may be snap-coupled, and at least one of spool 22 or handle 24 may form an internal channel to house at least a portion of coiled element 26. Coiled element 26 may be a guidewire, optical fiber, cautery element, or other medical element. In an aspect where coiled element 26 is a guidewire, the guidewire may be releasably coupled to spool 22. For example, the guidewire may be uncoiled from spool 22 and delivered within a patient. The guidewire may then be uncoupled from spool 22, and a medical device, for example, insertion device 12, may be positioned on the proximal portion of the uncoupled guidewire in order for the medical device to be delivered within the patient.

Spool 22 and handle 24 may be rotatably coupled such that relative rotation of spool 22 and handle 24 either dispenses or retracts coiled element 26 from the internal channel. Spool 22 may include a plurality of radially extending grip portions or knurls 48 on at least a portion of an outer circumferential surface of spool 22. Spool 22 and handle 24 may be mounted on adaptor 16, and adaptor 16 may ensure that handle 24 remains stationary as spool 22 is rotated. Spool 22 and handle 24 may be employed without adaptor 16, and the user's hand or fingers may ensure that handle 24 remains stationary as spool 22 is rotated. In one aspect, spool 22 and handle 24 may be formed of a transparent polymer, which may allow a user to see coiled element 26 within the internal channel to determine a length of the portion of coiled element 26 housed within the channel.

Adaptor 16 may be coupled to body 34 of insertion device 12 in order to couple medical device 14 to insertion device 12. Adaptor 16 may be coupled to intermediate portion 38 or proximal portion 40 of body 34. As shown in FIG. 1, adaptor 16 may be coupled to insertion device 12 on an opposite side of proximal portion 40 relative to longitudinal axis A from deflection lever 42. For example, adaptor 16 may be shaped to fit on insertion device 12 and match the contour of a portion of intermediate portion 38 and the wider proximal portion 40.

Adaptor 16 may also include a post 50 extending away from insertion device 12 when adaptor 16 is coupled to insertion device 12. Post 50 may be sized to fit through a central hole in medical device 14, for example, through handle 24, in order to securely attach medical device 14 to insertion device 12. It is noted that post 50 may include a rectangular, pentagonal, hexagonal, octagonal, or otherwise shaped post extension 52 that matches a central hole in handle 24 such that handle 24 may be secured relative to insertion device 12 while still allowing spool 22 to rotate in response to user action. As such, the shape of post 50 may prevent handle 24 from rotating while a user rotates spool 22.

In another aspect, post 50 may be tapered as it extends away from adaptor 16. A seat 54 may extend radially outward from post 50 in order to stop the vertical movement of medical device 14 on post 50. As such, a user may hold medical system 10 in one hand and both deflect a distal end of delivery shaft 20 through action on deflection lever 42 and also dispense or retract coiled element 26 through action on spool 22.

Figure 2:
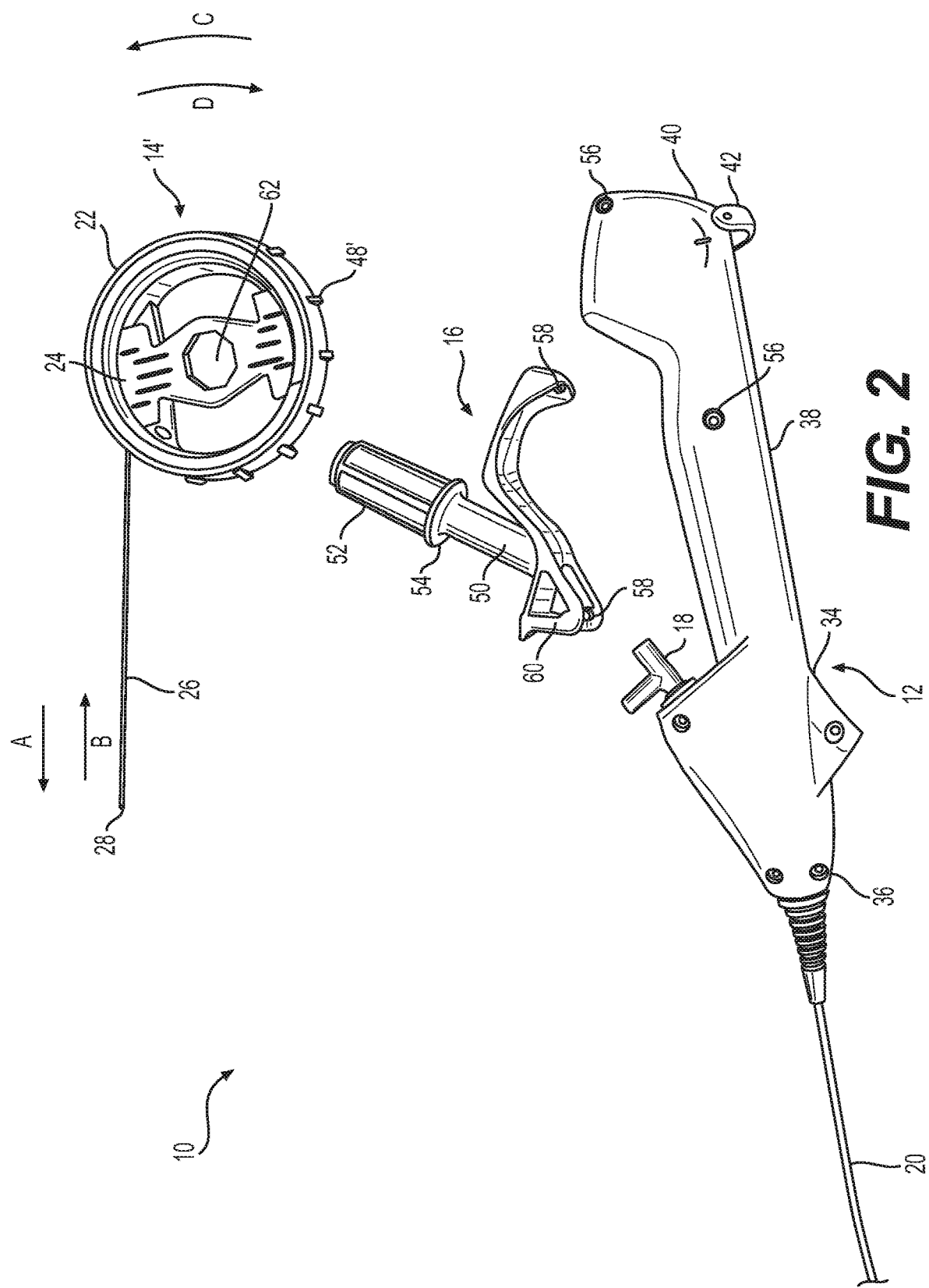
FIG. 2 illustrates a partially exploded view of the medical system of FIG. 1, according to aspects of the present disclosure.

FIG. 2 illustrates a partially exploded view of medical system 10 of FIG. 1. It is noted that FIG. 2 depicts medical device 14' with knurls 48', which may be larger or extend radially further than knurls 48 in FIG. 1 to aid a user in manipulating medical device 14'. As shown, insertion device 12 may include at least one indentation or hole 56, and adaptor 16 may include at least one adaptor pin 58. In one example, adaptor pins 58 may be positioned at distal and proximal positions to fit, snap, or otherwise secure into corresponding indentations or holes 56 in intermediate portion 38 or proximal portion 40 of insertion device 12. It is noted that holes 56 and adaptor pins 58 are shown on differing sides of insertion device 12 and adaptor 16 in FIG. 2, but holes 56 and adaptor pins 58 may be respectively positioned on both sides of insertion device 12 and adaptor 16. Adaptor 16 may also include biased or flexible extensions 60 that connect to at least one adaptor pin 58 such that extensions 60 may bend or flex as adaptor pins are positioned in holes 56 to couple adaptor 16 to insertion device 12.

Adaptor 16 may also include post extension 52 as part of post 50, and post extension 52 may be sized to fit within a central opening 62 within handle 24. For example, post extension 52 may be rectangular, pentagonal, hexagonal, octagonal, etc., and central opening 62 may include a corresponding shape. Alternatively, post extension 52 may include ridges to be received within grooves of central opening 62. Therefore, when mounted on adaptor 16, action on medical device 12 may rotate spool 22, while handle 24 remains stationary relative to insertion device 12. Moreover, post extension 52 may be sized to fit snugly within central opening 62, which may help to ensure that medical device 14' remains coupled to insertion device 12 via seat 54 of adaptor 16.

Seat 54 extends radially outward from post 50. Seat 54 is wider than central opening 62 in order to ensure that medical device 14' is positioned an appropriate distance from insertion device 12.

In use, a user may insert insertion device 12 into a patient through any known method. With adaptor 16 coupled to insertion device 12, a user may couple medical device 14 to insertion device 12. While holding insertion device 12 in one hand, a user may dispense coiled element 26 of medical device 14 in direction A through port 18 by rotating spool 22 in direction C with a finger of the one hand or with the user's other hand. A user may also retract coiled element 26 in direction B by rotating spool 22 in direction D. Knurls 48 may aid in the manipulation of spool 22. Coiled element 26 may be dispensed to the distal end of delivery shaft 20 such that distal end 28 of coiled element 26 may deliver therapy. Proximal end 30 of coiled element 26 may be coupled to another medical element. For example, coiled element 26 may be a laser fiber, and proximal end 30 may be coupled to a laser source (not shown). The user may quickly and easily maneuver the distal end of delivery shaft 20, for example, with action on deflection lever 42 with the user's thumb. The user may also maneuver coiled element 26, either extending distally or retracting proximally, by, for example, rotating spool 22 with the user's forefinger.

In another example, coiled element 26 may be a guidewire. Coiled element 26 may be dispensed from medical device 14 by rotating spool 22 relative to handle 24 such that coiled element 26 may be delivered and positioned within a patient. In this aspect, medical device 14 may be handheld, and separate from adaptor 16. Insertion device 12 may be inserted into a patient over coiled element 26. Once coiled element 26 emerges proximally from port 18, coiled element 26 may be inserted into medical device 14 by the user. The physical properties (e.g., elasticity) of coiled element 26 and/or internal slots or protrusions within medical device 14 may help to secure a proximal end of coiled element 26 within medical device 14. Then, rotation of spool 22 relative to handle 24 may help the user more quickly retract coiled element 26. Additionally, coiled element 26 may be stored within medical device 14 for later use in the procedure with the same patient. Alternatively, coiled element 26 may be pre-inserted through port 18 and extend out of the distal end of delivery shaft 20. Coiled element 26 may be delivered to the location within the patient. Insertion device 12 may then be inserted into patient and tracked over coiled element 26. As insertion device 12 is inserted, coiled element 26 may be retracted by rotating spool 22. Once insertion device 12 is positioned within the patient, coiled element 26 may be fully retracted by continuing to rotate spool 22.

In an additional example, medical device 14 may be mounted on insertion device 12 via adaptor 16. Medical device 14 may include coiled element 26 stored between spool 22 and handle 24. Insertion device 12 may be inserted into a patient, for example, into a patient urethra. Coiled element 26 may be delivered through port 18 and through a lumen in delivery shaft 20 by rotating spool 22. Coiled element 26 may be extended beyond a distal tip of delivery shaft 20. Using visualization and deflection capabilities of insertion device 12, a user may further extend and position coiled element 26. For example, a user may insert coiled element 26 into the ureteral orifice to access the patient's ureter. The user may further extend coiled element 26 through the patient's ureter, for example, into the patient's kidney. Fluoroscopy may be used to aid in the manipulation and positioning of coiled element 26. The user may then manipulate insertion device 12 to slide distally over coiled element 26 to access the ureter and the kidney. Once insertion device 12 is positioned, the user may retract coiled element 26 by rotating spool 22. Alternatively, the user may leave coiled element 26 inserted, and coiled element 26 may be dispensed and/or retracted as necessary during the procedure. Medical treatment may then be delivered to the patient's kidney through insertion device 12, or other medical devices may be introduced through insertion device 12 to deliver medical treatment. It is noted that a proximal portion of coiled element 26, for example, a portion of coiled element 26 extending from medical device 14 to port 18, may be held by a user's forefinger and thumb to maintain a position of coiled element 26 as insertion device 12 is inserted over the coiled element 26. Moreover, the user may rotate and/or torque coiled element 26 by manipulating the same proximal portion of coiled element 26. It is further noted that in the above description, coiled element 26 remains coupled to spool 22.

Figure 3B:
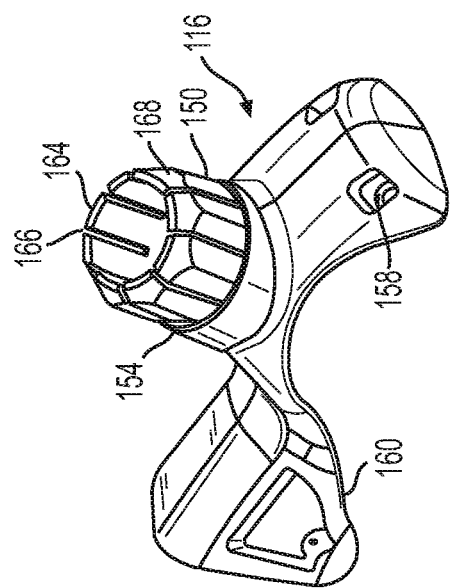
FIGS. 3A-3C illustrate different views of a medical device adaptor, according to aspects of the present disclosure.
Figure 3C:
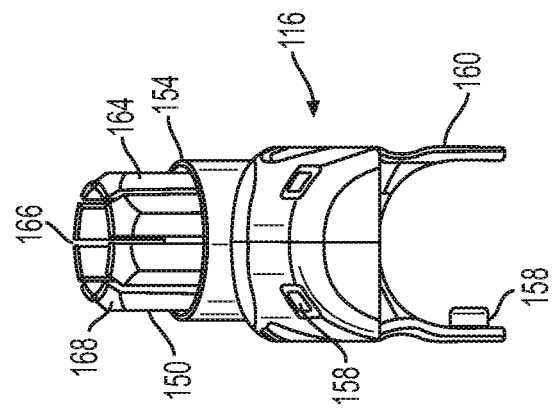
Figure 3A:
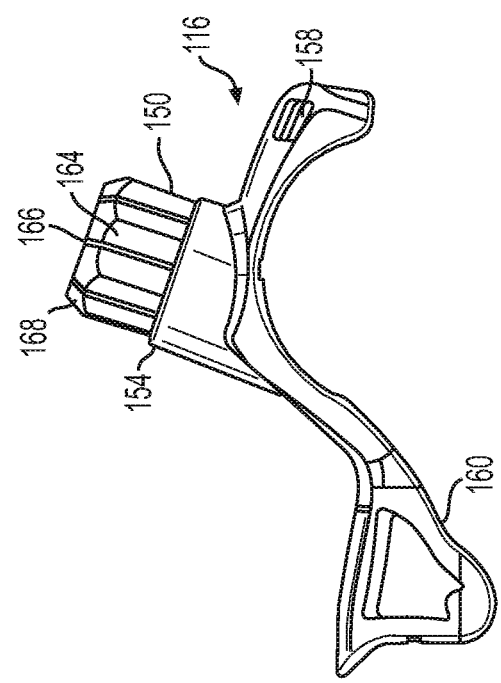

FIGS. 3A-3C illustrate an alternative adaptor 116 according to another aspect of this disclosure. FIG. 3A is a side view of adaptor 116. FIG. 3B is a perspective view of adaptor 116, and FIG. 3C is an end view of adaptor 116. Similar to adaptor 16, adaptor 116 may include at least one flexible extension 160 and at least one adaptor pin 158 to couple adaptor 116 to an insertion device via indentations or holes as discussed above. As shown in FIG. 3C, adaptor 116 may include an adaptor pin 158 on only one side of adaptor 116. In this instance, a user may rotate adaptor 116 toward the one adaptor pin 158 in order to remove adaptor 116 from the insertion device. Alternatively, adaptor 116 may include adaptor pins 158 on both sides of adaptor 116, which may affect the ease with which a user may couple and/or uncouple adaptor 116 to and from an insertion device. In another aspect, adaptor 116 may include straps, Velcro™, cables, twist ties, adhesive, or additional features to secure adaptor 116 to the insertion device. In the example shown in FIGS. 3A-3C, a post 150 may be positioned on a proximal portion of adaptor 116. As such, when coupled to an insertion device similar to insertion device 12, post 150 may extend from wider proximal portion 40.

Post 150 may also include seat 154 and a plurality of projections 164 with slots 166 positioned between projections 164. In one aspect, projections 164 may form the portion of adaptor 116 that is received within a central opening of a medical device 14. Each projection 164 may include a corner, with the corners of the projections 164 forming the shape to be received within the central opening. As shown in FIGS. 3A-3C, post 150 may include eight projections 164 to form an octagonal shape to be received within a central opening. Projections 164 may also be flexible such that projections 164 may bend radially inward as projections 164 are received within a central opening. Projections 164 may include chamfered portions 168 at a top portion of projections 164. Chamfered portions 168 may increase the ease with which a medical device may be inserted on adaptor 116.

Post 150 may be rigid, or may be flexible. In one aspect, post 150 may be angled to position a mounted medical device in a different position relative to the handle of an insertion device than that shown in FIG. 1. In another aspect, post 150 may include a flexible arm (not shown), which may bend and retain its shape for a user-customizable positioning.

Moreover, projections 164 on adaptor 116 may help allow a user to couple one or more medical devices to an insertion device as discussed above. For example, post 150 may extend a longer distance than that shown in FIGS. 3A-3C. Post 150 may extend a distance approximately equal to the thickness of two medical devices, three medical devices, etc. Moreover, a user may interchangeably mount different medical devices to an insertion device and selectively dispense or retract one or more coiled elements through the insertion device. Although not shown, post 150 may include one or more locking protrusions that may correspond to locking indentations (FIG. 5) in the handle of the medical device. Although not shown, projections 164 may include ramps extending radially outward from the radially outermost surface. In this aspect, central portion 62 of medical device 14 may engage the ramps of projections 164 as medical device 14 is coupled to adaptor 116, and the ramps may snap medical device 14 into place on adaptor 116. Ramps on projections 164 may help secure medical device 14 on adaptor 116. Medical device 14 may be uncoupled from adaptor 116, but additional force would be necessary to remove medical device 14 mounted on adaptor 116 without ramps because projections 164 would be squeezed together radially inward in order for central portion 62 to be disconnected from adaptor 116.

FIGS. 4A and 4B illustrate additional aspects of a medical device 214 that may be mounted on an insertion device via an adaptor 16, 116 as discussed above. Moreover, FIGS. 4A and 4B depict medical device 214 with a spool 222 and a handle 224 radially interior to spool 222. Spool 222 includes a plurality of knurls 248 on an outer circumferential surface. As discussed above, knurls 248 may allow a user to grip and rotate spool 222 to dispense or retract a coiled element. Spool 222 also includes a crank 270 positioned on a top, a bottom, or a lateral side of spool 222. FIGS. 4A and 4B illustrate a portion of crank 270. Crank 270 may allow a user to more quickly or efficiently rotate spool 222 relative to handle 224. Crank 270 may include a through-hole 272 extending through crank 270 and connecting to a channel within spool 222.

In one aspect, the coiled element (not shown) may pass proximally through through-hole 272. For example, a proximal portion of the coiled element may be positioned within an outer channel 273 of medical device 214. Outer channel 273 may be an indention or groove formed in an outer surface of either spool 222 or handle 224. Alternatively, outer channel 273 may be formed between spool 222 and handle 224 when spool 222 and handle 224 are coupled together. The user may unwind a portion of the proximal portion of the coiled element, e.g., a laser fiber, from outer channel 273 to a preferred length and then position the coiled element in through-hole 272. The coiled element may be proximally connected to another medical device (e.g., a laser source). Moreover, the coiled element may extend through through-hole 272 such that a portion of the coiled element that extends proximally to through-hole 272 does not get tangled or interfere with the user's rotation of spool 222.

Crank 270 may also include a slit 274 and/or a locking slot 276. Slit 274 may extend through a height of crank 274 such that a user may selectively position the coiled element within through-hole 272 or exterior to crank 270 altogether through a side slot 278 in spool 222. Side slot 278 may open into outer channel 273. Alternatively or additionally, a user may position the coiled element in locking slot 276. Locking slot 276 may extend through a portion of crank 270 parallel to slot 274, and may connect to slot 274 through side slot 278. Locking slot 276 includes a narrowing taper, which allows a user to lock a proximal portion of the coiled element in crank 270. The position of locking slot 276 and the stiffness or rigidity of the coiled element may help prevent the coiled element from rotating and/or becoming dislodged from its position in crank 270.

On an opposite side from crank 270, medical device 214 may include guide ramp 280 on a portion of handle 224. Guide ramp 280 may include a central lumen that connects to an internal channel within medical device 214 between spool 222 and handle 224. Medical device 214 may also include a tube support 282. Tube support 282 may also include a central lumen. As discussed in greater detail below, coiled element may be at least partially surrounded by a tube or sheath. Guide ramp 280 and tube support 282 may help guide coiled element, with or without an outer tube or sheath, as it is dispensed from or retracted into medical device 214.

Figure 5:
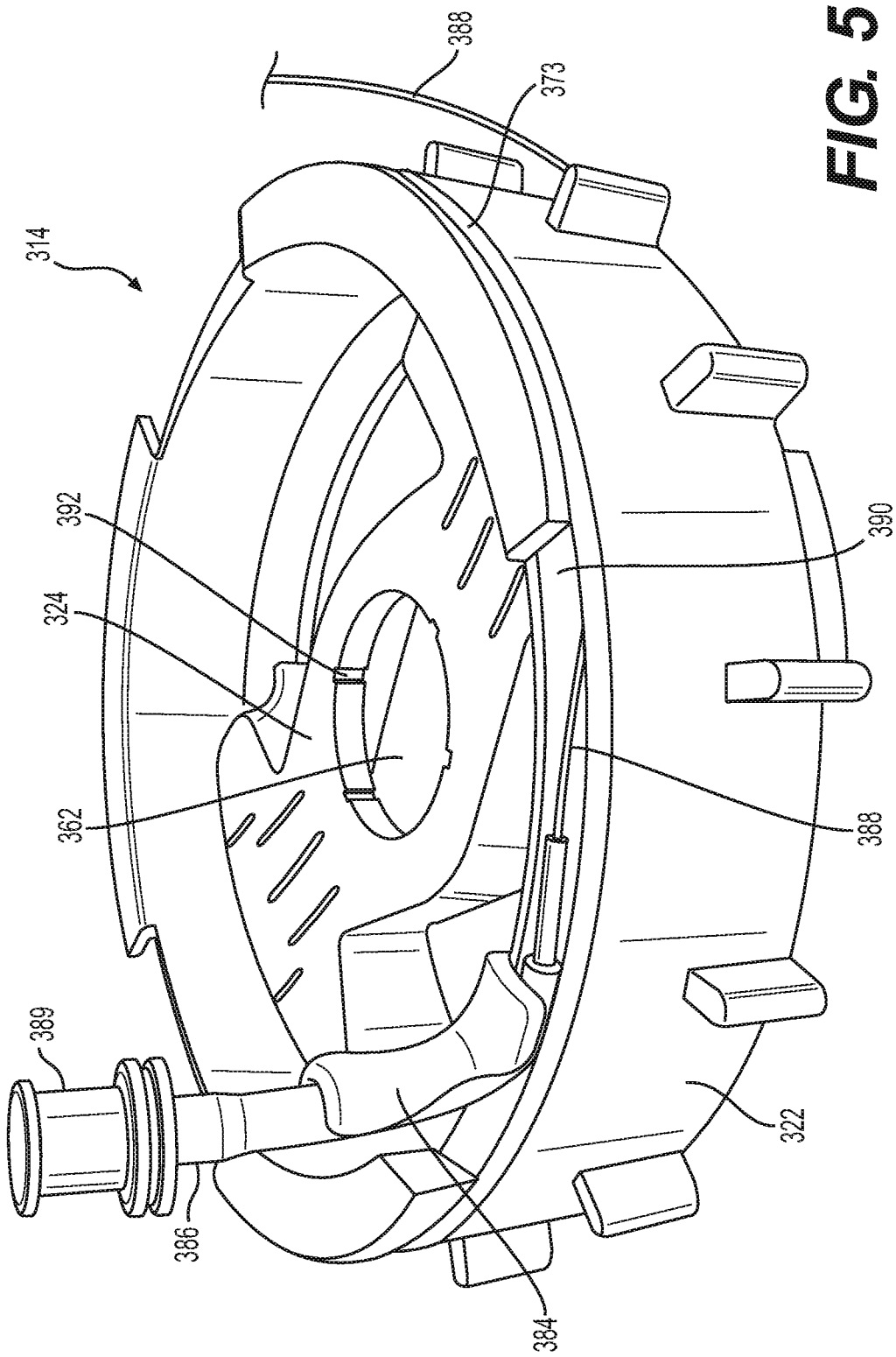
FIG. 5 illustrates a perspective view of a further medical device, according to aspects of the present disclosure.

FIG. 5 illustrates an additional aspect of this disclosure in a medical device 314. Medical device 314 includes a hub 384. Hub 384 may be positioned on a spool 322 similar to crank 270 in FIGS. 4A and 4B, and may also function similarly to crank 270 to more quickly or efficiently rotate spool 322 relative to handle 324. Hub 384 may support a medical element, such as, for example, a drainage catheter 386. Drainage catheter 386 may include a coiled element, such as, for example, a catheter shaft 388 that is coiled within a channel 390 between spool 322 and handle 324. Drainage catheter 386 may also include a drainage catheter hub 389. A user may couple medical device 314 to an insertion device via an adaptor as discussed above.

It is noted that FIG. 5 illustrates a plurality of locking indentations 392 in a central opening 362 in handle 324, which may correspond to locking protrusions on an adaptor to lockably couple handle 324 to the adaptor and ensure that handle 324 does not rotate when a user rotates spool 322. The user may rapidly dispense catheter shaft 388 by rotating spool 322. Once positioned within the patient, the user may activate drainage catheter 386. The user may reposition the distal end of catheter shaft 388 by deflecting the delivery shaft, or may retract catheter shaft 388 by rotating spool 322 relative to handle 324 to remove drainage catheter 386 from the patient. The user may repeat the above steps in order to introduce a different medical device, such as, for example, an additional drainage catheter, by coupling the other medical device to the insertion device via an adaptor.

In one aspect, a user may connect an extension tube to drainage catheter hub 389 to connect drainage catheter 386 to a drainage bag. In another aspect, a proximal portion of catheter shaft 388 may be coiled around a radially external portion of spool 322, for example, within an outer channel 373, as discussed above with respect to FIGS. 4A and 4B. In this instance, drainage catheter 386 may be disengaged from hub 384, and the user may extend drainage catheter 386 proximally to connect drainage catheter hub 389 directly to a drainage bag. The proximal portion of catheter shaft 388 coiled around spool 322 may unwind as drainage catheter 386 is extended proximally, which may provide a slack or surplus amount of catheter shaft 388 necessary for drainage catheter 386 to extend to couple drainage catheter hub 389 to the drainage bag.

Figure 6:
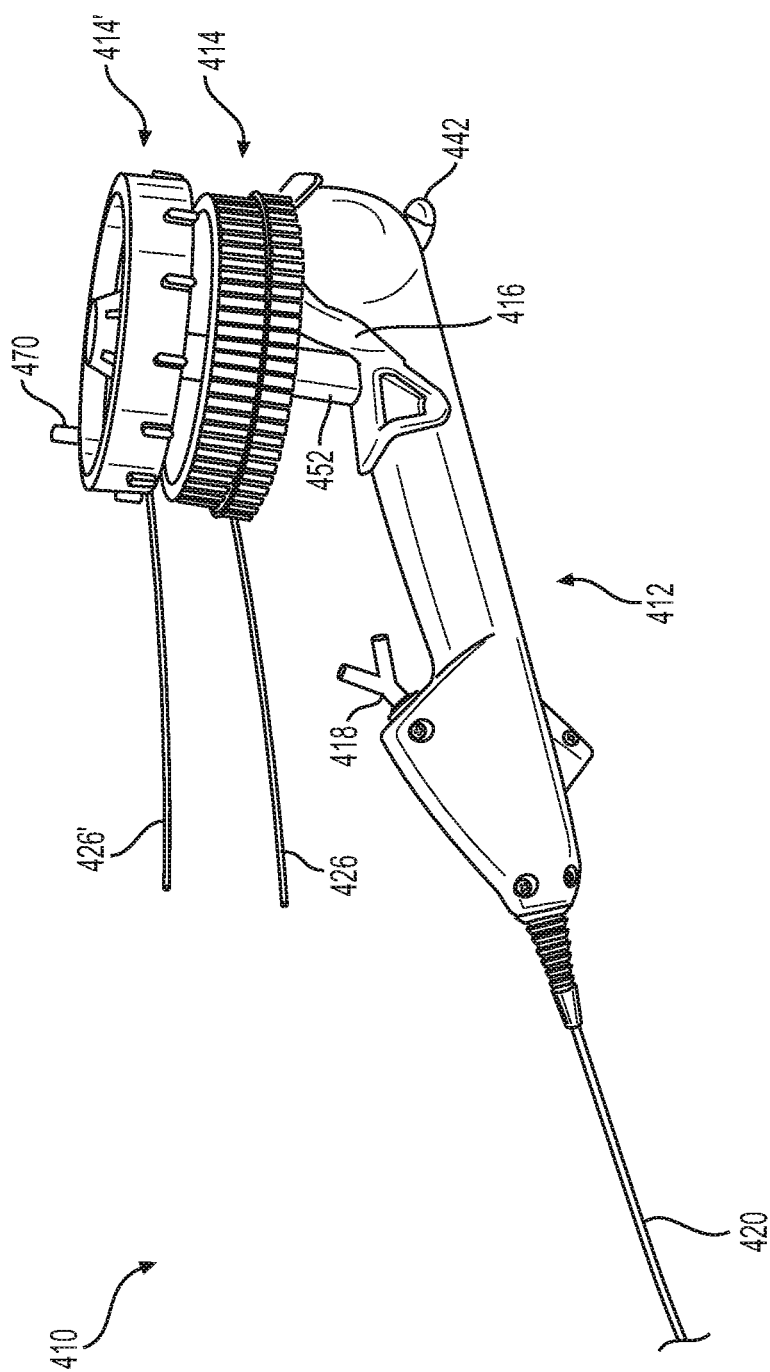
FIG. 6 illustrates an additional medical system, according to aspects of the present disclosure.

FIG. 6 illustrates a medical system 410 according to additional aspect of this disclosure where two medical devices 414 and 414' are both coupled to an insertion device 412 via an adaptor 416. Adaptor 416 includes a post extension 452 that extends through the central openings of the handles of medical devices 414 and 414'. In one aspect, post extension 452 may include a particular shape or locking protrusions to correspond to the central openings of the handles of medical devices 414 and 414'. In another aspect, post extension 452 may include a taper or differently sized portions to correspond to different sized central openings of the handles of medical devices 414 and 414'. In one example, a medical device 414 with a wider central opening may be positioned on a bottom portion of post extension 452, and a medical device 414' with a narrower central opening may be positioned on a top portion of post extension 452.

Coiled elements 426 and 426' may extend from medical devices 414 and 414', and may be individually or both introduced through port 418 of insertion device 412, for example, through different portions of port 418. A user may then hold insertion device 412 such that his or her thumb may activate deflection lever 442. The user's forefinger or other hand may rotate one or both of medical devices 414 and 414' to extend or retract coiled elements 426 and 426'. In one example, medical device 414' may include a crank 470, which may aid in a user more rapidly extending or retracting coiled element 426'. Therefore, a user may selectively extend and retract a guidewire and a retrieval device. In an alternative example, a user may selectively extend and retract an optical fiber and a retrieval device. The user may also extend and retract the elements while also deflecting the distal end of delivery shaft 420 through deflection lever 442.

FIGS. 7A-7C illustrate an additional aspect of this disclosure with a universal adaptor 594 and a medical device 514. FIG. 7A is a perspective view of universal adaptor 594 and medical device 514. FIG. 7B is a side view of universal adaptor 594 coupled to medical device 514, and FIG. 7C is an end view. Universal adaptor 594 may couple medical device 514 to a handle of a different insertion device or to a separate medical element, such as, for example, a surgical table or a curtain. Universal adaptor 594 includes holes or eyelets 596, which may receive one or more straps or other connection elements in order to couple universal adaptor 594 and medical device 514 to any handle or medical element. As seen in FIG. 7C, a post support 598 may extend from universal adaptor 594 to couple medical device 514 to universal adaptor 594 and orient medical device 514 parallel to the vertical plane of universal adaptor 594. Post support 598 includes a post 550 which passes through a central opening 562 of a handle 524 of medical device 514 as discussed above. The user may rotate spool 522 to extend or retract a coiled element (not shown), with medical device 514 secured to an insertion device handle or other medical element. Additionally, spool 522 may also include a crank 570, which may increase the rate at which the user may extend or retract the coiled element.

Although not shown, universal adaptor 594 may be coupled to or integrally formed with an endoscope or another insertion device (e.g., Spyglass® Direct Visualization System by Boston Scientific Corp.) to couple medical devices to the insertion device. In another aspect, multiple universal adaptors 594 may be coupled to an insertion device or other medical element used in a procedure to allow a user to dispense and retract multiple medical devices during the procedure.

Turning now to FIGS. 8-11, the figures illustrate an additional aspect of this disclosure. The figures disclose a medical device 614 that may be coupled to an insertion device via an adaptor as discussed in any of the embodiments disclosed above. Medical device 614 may allow a user to dispense or retract a coiled element. Medical device 614 may also allow a user to control an extension of an end effector from a sheath and/or to control the opening and closing of an end effector, such as, for example, a self-expandable retrieval basket.

Figure 8:
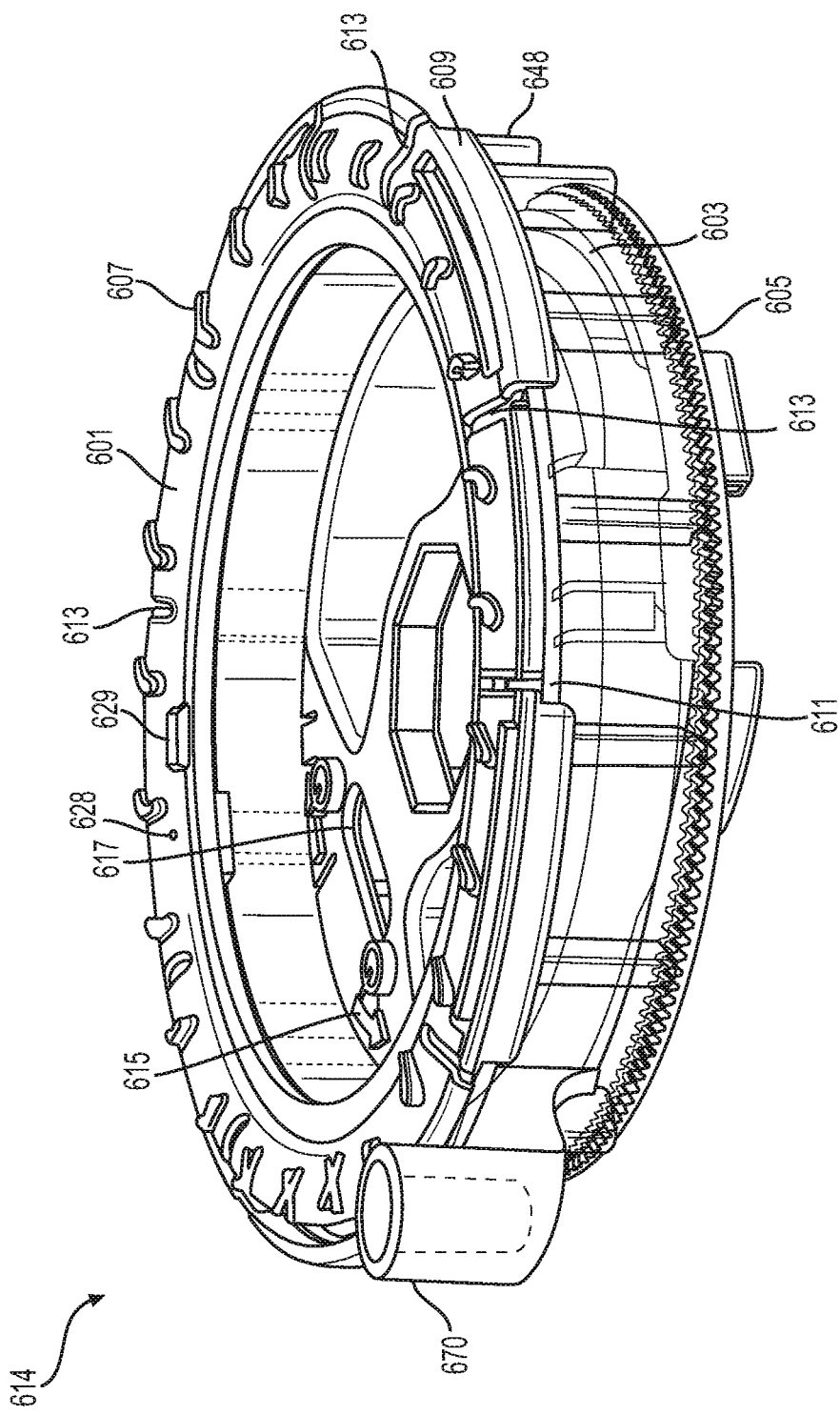
FIG. 8 illustrates a further exemplary medical device, according to aspects of the present disclosure.

FIG. 8 is a perspective view of a top portion of medical device 614. As shown in FIG. 8, medical device 614 includes a control knob 601, a spool 603, and a handle 605. It is noted that medical device 614 may be coupled to an insertion device via an adaptor in a configuration such that control knob 601 is accessible to the user, such as, for example, on the top of medical device 614 as medical device 14 is shown in FIG. 1. FIG. 8 also shows crank 670 extending away from spool 603. Control knob 601 may include grips 607 on a top surface of control knob 601. Control knob 601 may include snap locks 609 to allow control knob 601 to be rotatably coupled to spool 603 via a corresponding ledge 611 on spool 603. Control knob 601 also includes a plurality of relief slots 613, which allow snap locks 609 to flex for control knob 601 to be coupled to spool 603.

Medical device 614 may be coupled to an adaptor on an insertion device as discussed in the embodiments above. A user may rotate spool 603 to dispense a coiled element (not shown), either by action on knurls 648 or crank 670. Handle 605 may include one or more indications 615 to provide the user with visual indications as to the relative rotation directions to extend or retract the coiled element. Handle 605 may also include hemostat holes 617. Hemostat holes 617 may be at least partially oval shaped and may allow for handle 605 to be coupled to a hemostat to secure medical device 614 during a procedure. For example, hemostat holes 617 may allow medical device 614 to be securely coupled to a drape, an IV pole, or another surface or structure in the procedure. The finger rings of the hemostat may help retain medical device 614, and the partially oval shape may help prevent handle 605 from rotating when spool 603 is rotated.

A drive wire and a sheath may be coupled to control knob 601, and movement of control knob 601 relative to spool 603 extends or retracts the drive wire or the sheath. For example, although not shown in FIG. 8, control knob 601 may include a block that is rotatably movable within a groove within spool 603, and the drive wire and the sheath may be coupled to control knob 601 or within the groove to selectively extend or retract the drive wire. As shown in FIG. 8, control knob 601 may include a hole 628 within the block and through control knob 601 to allow a proximal portion of the drive wire to extend proximally of control knob 601. Control knob 601 may also include one or more biased projections or clips 629 to secure the proximal portion of the drive wire that extends proximally of control knob 601. Multiple blocks, holes 628, and clips 629 may be positioned on control knob 601 to allow a user to selectively lock a proximal portion of the drive wire in different positions on control knob 601. Alternatively, the drive wire and/or the sheath may be coupled to control knob 601 or spool 603 via glue or other adhesives.

In one aspect, the coiled element may include an end effector and a drive wire surrounded by a sheath, with both the drive wire and the sheath coupled to portions of medical device 614. For example, the drive wire may be coupled to control knob 601, and the sheath may be coupled to spool 603. The user may then rotate control knob 601 relative to spool 603 and handle 605 to extend or retract the end effector relative to a distal end of the sheath. The end effector may be a retrieval device (e.g., expandable basket), a cautery instrument, or another sheathed device. Therefore, because the sheath is fixed relative to spool 603, rotation of control knob 601 relative to spool 603 extends the drive wire of the coiled element distally beyond the sheath, for example, to expand an expandable retrieval basket. Alternatively, the sheath may be attached to control knob 601, and the drive wire of the coiled element may be fixed relative to spool 603. In this aspect, relative rotation of control knob 601 relative to spool 603 may retract the sheath, which in turn may cause the expandable retrieval basket to expand. In any of the above examples, indications 615 may indicate to a user the direction of rotation necessary to expand the retrieval basket.

Figure 9:
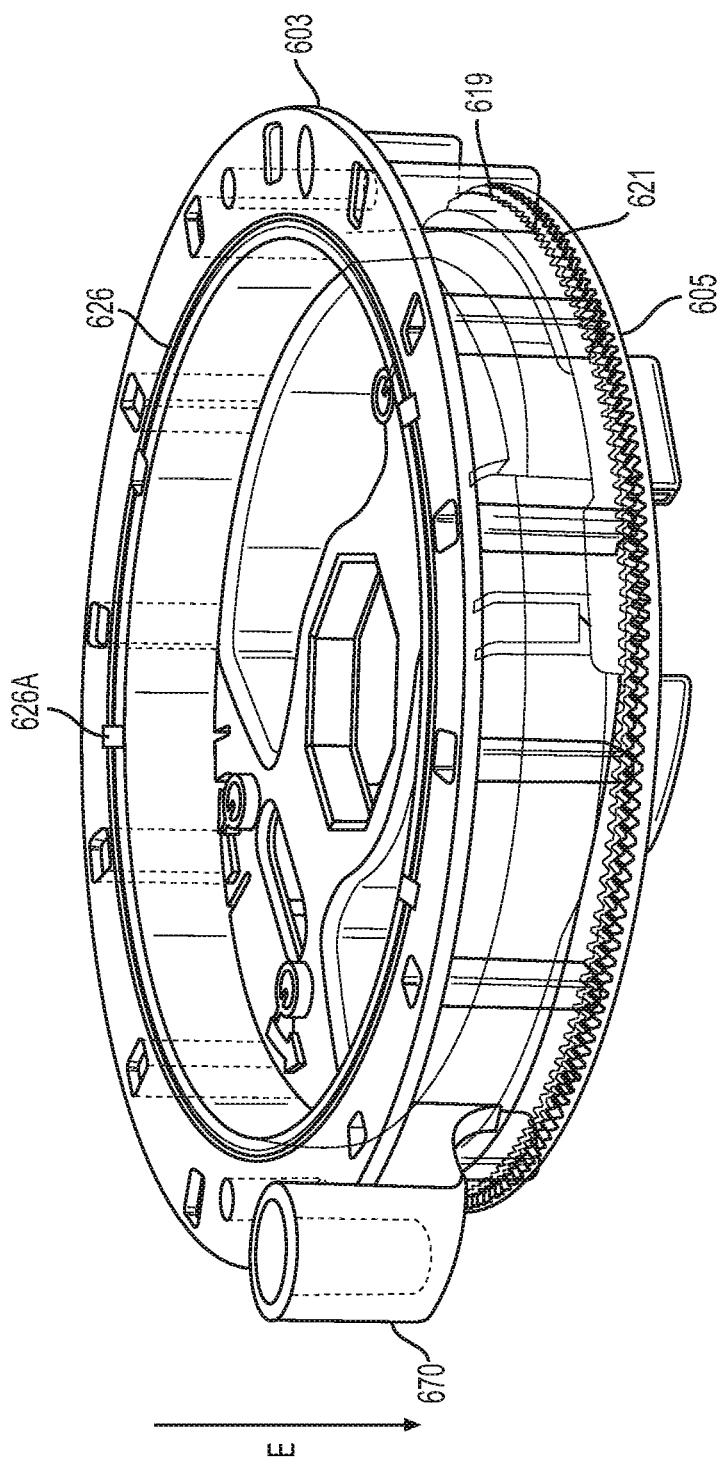
FIG. 9 illustrates a perspective view of a portion of the medical device of FIG. 8, according to additional aspects of the present disclosure.

FIG. 9 is a perspective view of medical device 614 with control knob 601 removed. Spool 603 may include a groove 626 in the surface of spool 603 facing control knob 601. Groove 626 connects to the channel between or within one of spool 603 and handle 605 such that the coiled element may extend through both groove 626 and the channel.

Groove 626 may be a generally rectangular cutout in the surface of spool 603, and may extend circularly around spool 603. Groove 626 may include a plurality of U-ribs or stop surfaces 626A that decrease the width or cross-sectional area of groove 626. The U-ribs or stop surfaces 626A may be U-shaped or another appropriate shape indentation toward the center of groove 626 forming a narrower portion. In another aspect, stop surfaces 626A may be enclosed or blocked portions of groove 626 with a through-hole extending through the enclosed or blocked portion to allow the drive wire to extend through the stop surface 26A. Stop surfaces 626A may aid in coupling and/or limiting the movement of one of the elements within groove 626. In another aspect, groove 626 may include a plurality of grooves distributed around the top surface of spool 603 and connecting to the channel between spool 603 and handle 605. The plurality of grooves may be different lengths and configurations, which may provide for different coiled elements, e.g., different types of expandable baskets, to be coupled and actuated with medical device 614. As mentioned, one of a drive wire or a sheath may be coupled to spool 603, for example, within groove 626, with the other of the drive wire or sheath coupled to control knob 601. Portions of control knob 601 may extend into and slide within groove 626, with stop surfaces 626A limiting the movement of control knob 601.

As shown in FIG. 9, spool 603 and handle 605 are coupled as discussed above with the addition of spool teeth 619 and handle teeth 621 at the circumferential junction of spool 603 and handle 605. Spool teeth 619 and handle teeth 621 may be distributed over 360 degrees of the respective components, or only over a portion of the circumferential junction. Spool teeth 619 and handle teeth 621 may be offset, for example, by approximately 180 degrees. Spool teeth 619 and handle teeth 621 may be triangular, square, or another shape. Although not shown, one or more wave springs, cantilevered springs, or other biasing members may be positioned between spool teeth 619 and handle teeth 621 to bias the mating of spool teeth 619 and handle teeth 621.

In one aspect, one or both of spool teeth 619 and handle teeth 621 may include cantilevered tabs that bias the compression of spool 603 toward handle 605 rather than a separate spring element. Because the mating of spool teeth 619 and handle teeth 621 is biased by the biasing member, spool 603 may rotate freely relative to handle 605 when spool 603 is not compressed toward handle 605 such that spool teeth 619 do not mate with handle teeth 621. If spool 603 is compressed toward handle 605 in direction E, then spool teeth 619 engage with handle teeth 621. Therefore, if a user compresses medical device 614 by depressing control knob 601 in direction E, the user may compress spool teeth 619 and handle teeth 621, locking the elements together, and then rotate control knob 601 relative to locked spool 603 and handle 605. The compression and rotation of control knob 601 may allow the user to extend or retract the drive wire coupled to control knob 601 relative to the sheath coupled to spool 603.

Figure 10:
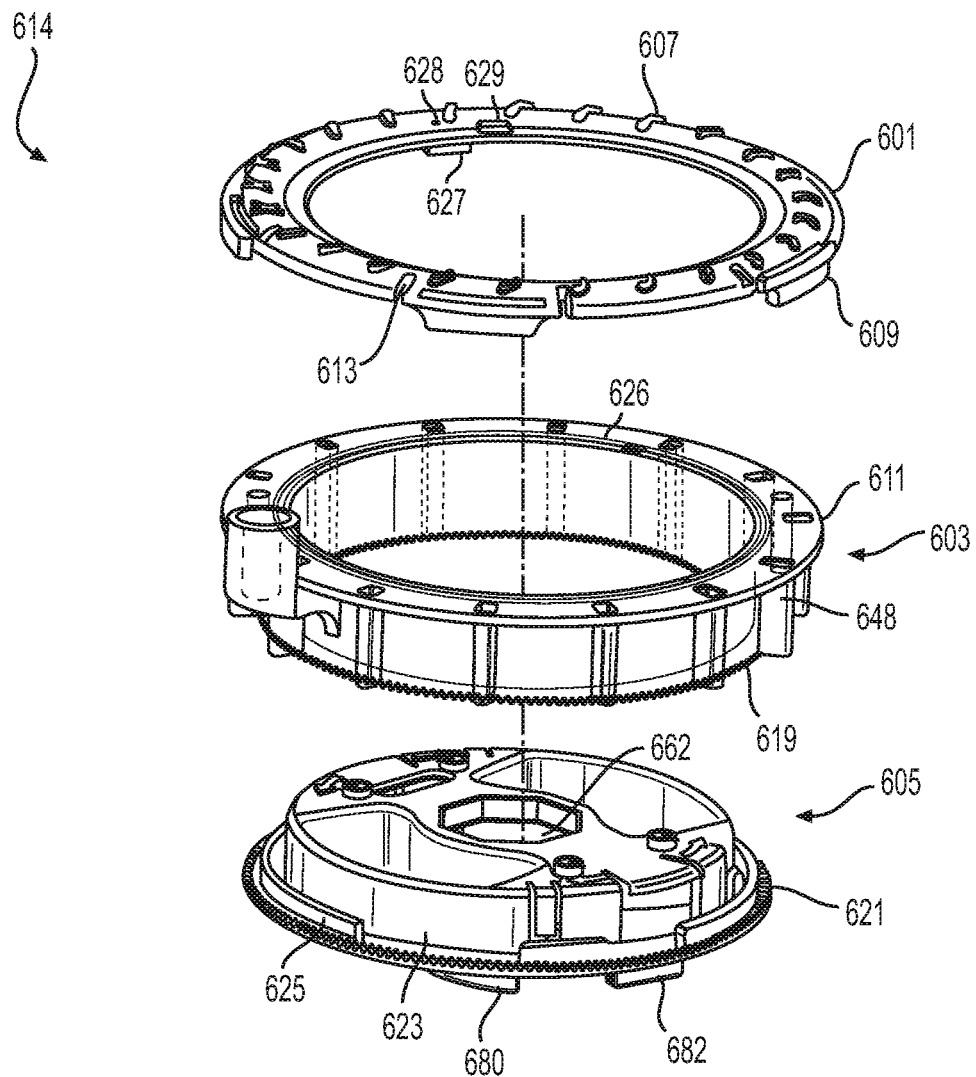
FIG. 10 illustrates an exploded view of the medical device of FIG. 8, according to additional aspects of the present disclosure.

FIG. 10 is an exploded view of medical device 614. Control knob 601 includes snap lock 609 with relief slots 613 to rotatably couple control knob 601 to spool 603. Control knob 601 may include grips 607. Control knob 601 also includes block 627 with passage or hole 628 extending through block 627 and control knob 601. Control knob 601 may include clip 629 to selectively lock a proximal portion of the drive wire relative to control knob 601.

Spool 603 includes ledge 611 and spool teeth 619. Spool 603 may include one or more knurls 648. As discussed above and shown in FIG. 10, spool 603 includes groove 626, and block 627 may be positioned and slide within groove 626 as control knob 601 rotates relative to spool 603. Although not shown, a wave spring, cantilevered spring, or other biasing element is positioned between spool teeth 619 and handle teeth 621. Additionally, spool 603 may include an inner cylindrical wall 671 and an outer cylindrical wall 673, with a channel 675 between the two cylindrical walls forming an inner channel to house the coiled element (FIG. 11B).

Handle 605 includes a handle body 623 and one or more channel extensions 625. Handle 605 may be rotatably snap-coupled to spool 603, and channel extensions 625 may cap off, extend into, or otherwise cover channel 675 formed by inner cylindrical wall 671 and outer cylindrical wall 673 of spool 603. Channel extensions 625 may help to prevent the coiled element from escaping from channel 675. For example, channel extensions 625 may reduce or prevent a gap from forming between spool 603 and handle 605 and into channel 675 in the event that spool 603 and handle 605 were to partially separate. Circular extensions 625 are shown as a plurality of extensions, but may also be one single extension that spans the circumference of spool 603. Handle 605 may also include a central opening 662 to couple medical device 614 to an adaptor.

Handle 605 may include a guide ramp 680 and a tube support 682. Guide ramp 680 may help direct the coiled element into and out of the channel between spool 603 and handle 605. Tube support 682 may help direct the coiled element toward guide ramp 680 or away from guide ramp 680.

Figure 11A:
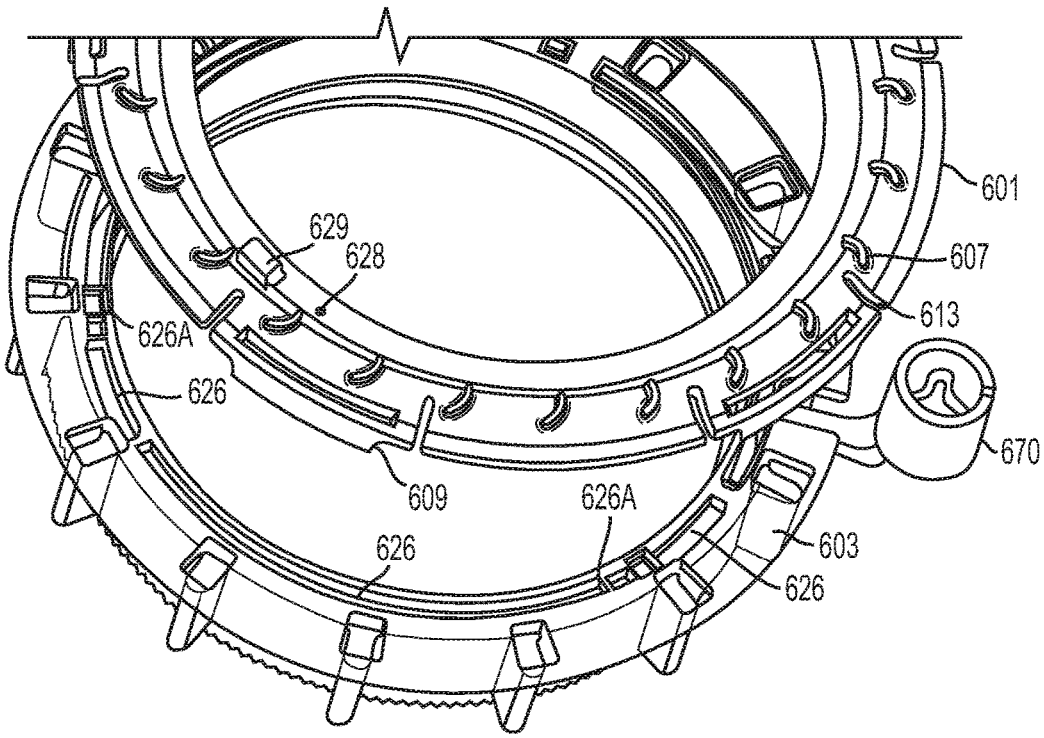
FIGS. 11A and 11B illustrate perspective and exploded views of portions of the medical device of FIG. 8, according to additional aspects of the present disclosure.
Figure 11B:
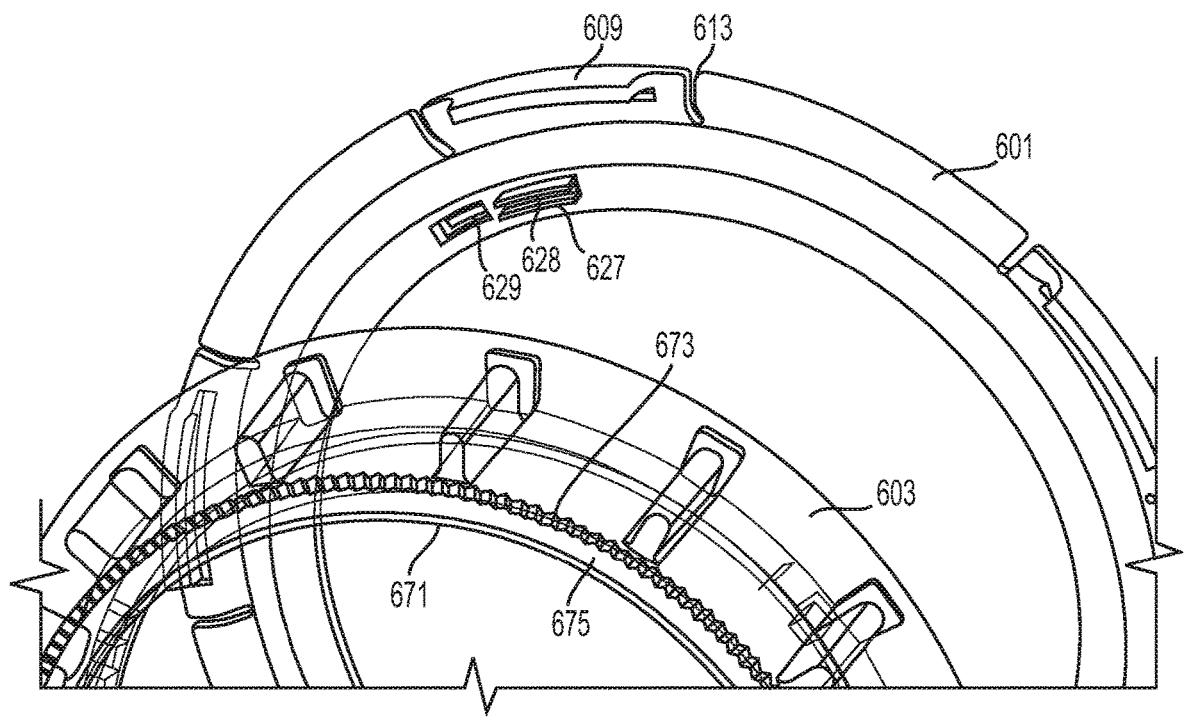

FIGS. 11A and 11B illustrate additional details of control knob 601 and spool 603. As mentioned, spool 603 includes grooves 626 with stop surfaces 626A. Control knob 601 includes a block 627 with passage or hole 628. Block 627 may be sized to fit and move within one of grooves 626 between stop surfaces 626A. Control knob 601 may also include clip 629 such that a drive wire may pass through hole 628 and be securely coupled to control knob 601. A sheath may be attached to spool 603 via one of stop surfaces 626A. Alternatively, the drive wire may be coupled to spool 603, and the sheath may be coupled to control knob 601. Therefore, movement of control knob 601 relative to spool 603 extends or retracts the drive wire or the sheath, with the other element fixed.

It is noted that the drive wire and sheath of the coiled element may loop or form a helix within channel 675 formed spool 603 several times in a fully retracted position. Moreover, as the coiled element is dispensed, the drive wire and sheath of the coiled element are dispensed at the same rate.

Once the coiled element is dispensed to a desired position within the patient, the user may compress the medical device via control knob 601 such that spool teeth 619 engage with handle teeth 621. The user may then rotate control knob 601 relative to spool 603, with spool 603 locked with handle 605 in order to extend or retract the drive wire relative to the sheath, or vice versa.

In one aspect, a sheath may be secured to a portion of groove 626. For example, a sheath may be glued to a portion of groove 626, or the sheath may have an enlarged portion that is secured on one of stop surfaces 626A or between two stop surfaces 626A, fixing the sheath relative to spool 603. The drive wire may extend proximally of the proximal end of the sheath. The drive wire may extend through block 627, through hole 628, and be secured via clip 629, fixing the drive wire relative to control knob 601. Rotation of control knob 601 relative to spool 603 advances the drive wire distally or retracts the drive wire proximally relative to the fixed sheath.

In another aspect, the drive wire may be fixed to spool 603 within groove 626, for example, at a position proximal of block 627, fixing the drive wire relative to spool 603. The sheath may be coupled to block 627, fixing the sheath relative to control knob 601. Rotation of control knob 601 relative to spool 603 retracts the sheath distally or extends the sheath proximally relative to the fixed drive wire. Similar to as above, if the drive wire includes an expandable retrieval basket, the basket may expand and contract as the sheath retracts proximally and extends distally.

Moreover, with control knob 601 rotated relative to spool 603, a user may release the compression to uncouple spool teeth 619 from handle teeth 621. The user may then further dispense or retract the coiled element with the end effector extended. It is noted that control knob 601, spool 603, and handle 605 may be varied or include various features such that the medical device 614 may include different end effectors disposed within a sheath.

Grooves 626 and stop surfaces 626A of spool 603 may also serve as one or more stroke limiters. The stroke limiters may limit the rotation of control knob 601 relative to spool 603. Block 627 on control knob 601 extends into groove 626, and stop surfaces 626A may restrict the movement of block 627, and thus restrict the rotation of control knob 601 relative to spool 603. As such, groove 626 and block 627 limit the distal movement of the drive wire relative to the sheath. Alternatively, groove 626 and block 627 may limit the proximal movement of the sheath relative to the drive wire. Furthermore, a biasing member or a spring may be positioned within a portion of groove 626, for example, distal to block 627 and proximal to a stop surface 626A, to bias the movement of control knob 601 relative to spool 603, and thus bias the relative movement of the drive wire and the sheath.

FIGS. 12A-12F illustrate additional aspects that may be incorporated in medical device 614. Specifically, FIGS. 12A-12F are linear representations of the proximal end of various end effectors that may be incorporated in medical device 614. The various end effectors are generally referred to as end effectors 700A-700F, with the variations discussed below. For example, if viewed from a top view, the figures would illustrate a curved configuration that matches the curved configuration of the channel formed between spool 603 and handle 605. FIGS. 12A-12F illustrate end effectors 700A-700F in closed configurations, and with drive wires 731A-731F lockably coupled to control knob 601 through one of block 627, hole 628, and clip 629. Drive wires 731A-731F are at least partially surrounded by respective sheaths 733A-733F. It is noted that different block 627 and clip 629 arrangements may be used for different end effectors, for example, to lockably position the drive wires 731A-731F of the end effectors 700A-700F varying distances from the proximal end of sheaths 733A-733F. Moreover, the connections to block 627 for the below discussion are illustrated in the figures as rectangular blocks 735A-735F. However, the movement of the respective rectangular blocks 735A-735F in the figures is understood to represent the movement of block 627 within groove 626, and thus the rotation of control knob 601 relative to spool 603.

Figure 12A:
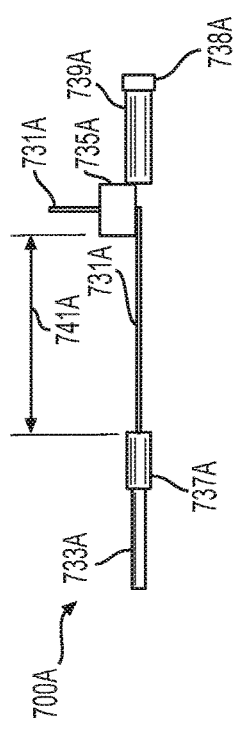
FIGS. 12A-12F illustrate various aspects that may be incorporated in any of the aforementioned medical devices, according to aspects of the present disclosure.

FIG. 12A illustrates a proximal portion of an end effector assembly 700A that includes drive wire 731A and sheath 733A. Drive wire 731A is proximally secured to a control knob 601 and passes through block 735A. Sheath 733A is coupled to spool 603. For example, sheath 733A may include a sheath extension 737A that is glued within a portion of groove 626A. End effector assembly 700A may also include a U-rib or stop surface 738A and a proximal stroke limiter 739A proximal of block 735A. Proximal stroke limiter 739A may decrease a distance block 735A may move proximally, and thus limit a distance block 627 may move within groove 626. The distance between proximal stroke limiter 739A and sheath extension 737A may define a stroke length 741A, or a distance which control knob 601 may move relative to spool 603, and thus a distance drive wire 731A may move relative to sheath 733A. Therefore, once the coiled element is dispensed to the desired location, the user may compress medical device 614 and rotate control knob 601 to extend a distal end of drive wire 731A of end effector assembly 700A from sheath 733A. The user may then manually rotate control knob 601 in the opposite direction to retract the distal end of drive wire 731A of end effector assembly 700A into sheath 733A.

Figure 12B:
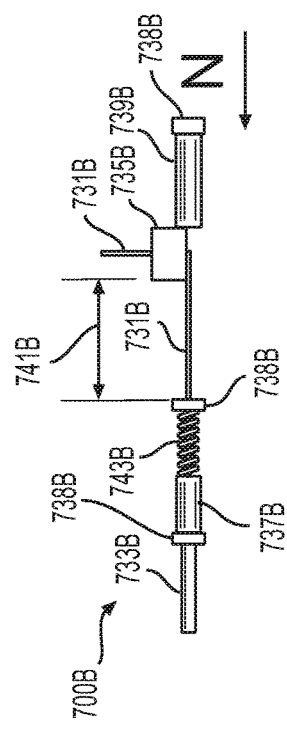

FIG. 12B illustrates a proximal portion of an end effector assembly 700B that includes drive wire 731B and sheath 733B. Drive wire 731B is proximally connected to control knob 601 as discussed above, through block 735B. Sheath 733B is positioned within groove 626. Sheath 733B includes a sheath extension 737B that may be slidable between two U-ribs or stop surfaces 738B. End effector assembly 700B may also include a proximal stroke limiter 739B. The distance between proximal stroke limiter 739A and one stop surface 738B may define a stroke length 741B, or a distance which control knob 601 may move relative to spool 603, and thus a distance drive wire 731B may move relative to sheath 733B. End effector assembly 700B may also include a spring 743B positioned between sheath extension 737B and one of stop surfaces 738B. Therefore, once the coiled element is dispensed to the desired location, the user may compress medical device 614 and rotate control knob 601 to move drive wire 731B in direction N to extend a distal end of drive wire 731B of end effector assembly 700B from sheath 733B. The user may rotate control knob 601 in the opposite direction to retract drive wire 731B within sheath 733B. However, sheath 733B may also retract proximally with sheath extension 737A compressing spring 743B. For example, sheath 733B may retract proximally if a stone or other material retrieved with an expandable basket is too large to fit within sheath 733B. As such, end effector assembly 700B may reduce the stress on sheath 733B when retracting a large stone or piece of material, which may decrease the likelihood of sheath 733B damage or malfunction.

Figure 12C:
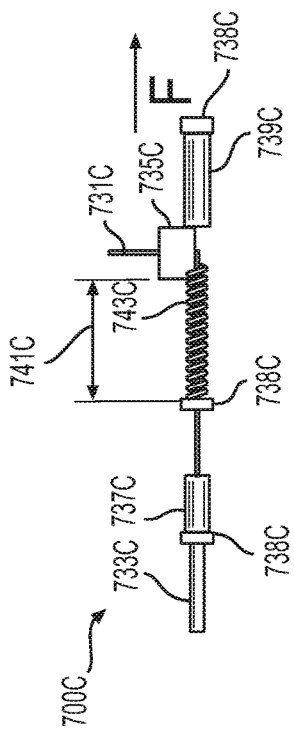

FIG. 12C illustrates a proximal portion of an end effector assembly 700C. In this aspect, a spring 743C may be coupled between block 735C and an stop surface 738C proximal of sheath 733C and sheath extension 737C. Therefore, spring 743C may bias the rotation of control knob 601 and thus provide a force in direction F against the movement of drive wire 731C. The distance between block 735C and the stop surface 738C that supports spring 743C defines a biased stroke length 741C. In this aspect, sheath extension 737C may be glued within groove 626 at one of the stop surfaces 738C, or sheath extension 737C may be movable between two stop surfaces 738C as discussed above. Spring 743C may help retract drive wire 731C proximally, and thus rotate control knob 601 relative to spool 603, without user activation.

Figure 12D:
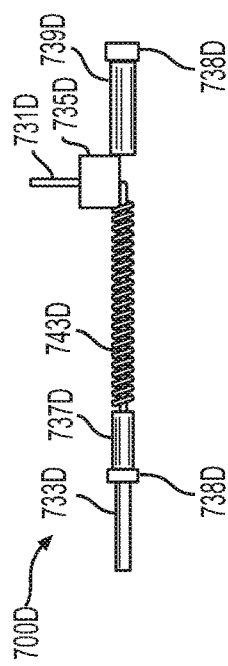

FIG. 12D illustrates a proximal portion of an end effector assembly 700D. In this aspect, spring 743D may be positioned between block 735D and sheath extension 737D. As discussed above, spring 743D biases the distal movement of block 735D, and thus the distal extension of drive wire 731A between a stroke length 741A between proximal stroke limiter 739A and sheath extension 737D. Sheath extension 737D may be stopped distally by a distal stop surface 738D, but may be free to move proximally. Proximal movement of sheath 733D and sheath extension 737D is also biased by spring 743D, which may help to prevent damage or malfunctioning of sheath 733D as discussed above. In an alternative aspect, end effector assembly 700D may be implemented without spring 743D, such that sheath 733D and sheath extension 737D may move proximally without spring bias in the case where the stone or material captured by the expandable basket coupled to drive wire 731A is too large.

Figure 12E:
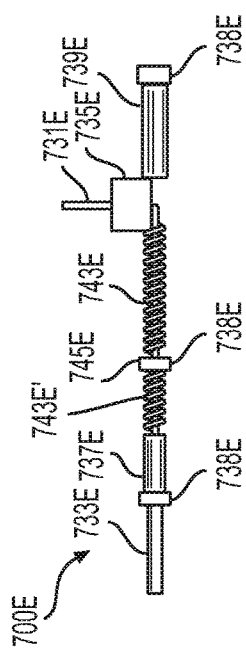

FIG. 12E is similar to FIGS. 12B and 12C. In this aspect, end effector assembly 700E may include a spring 743E positioned between block 735E and an intermediate stop surface 738E positioned proximal to sheath extension 737E. Spring 743E may bias the movement of drive wire 731E between proximal stroke limiter 739E and intermediate stop surface 738E. End effector assembly 700E may also include a spring 743E' positioned between sheath extension 737E and intermediate stop surface 738E. Spring 743E' may bias any movement of sheath 733E and sheath extension 737E if, for example, drive wire 731E captures a large stone, as discussed above.

Figure 12F:
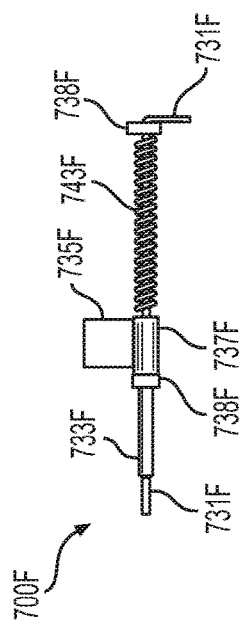

FIG. 12F illustrates an end effector assembly 700F with drive wire 731F passing proximally of block 735F and coupled via a proximal stop surface 738F to spool 603. Sheath 733F and sheath extension 737F are coupled to block 735F, and thus movable with control knob 601. A distal stop surface 738F may serve as a distal limiter for sheath extension 737F, and a spring 743F may bias the proximal movement of block 735F and sheath 733F. As such, a user may rotate control knob 601 proximally in order to retract sheath 733F, which unsheathes the distal end of drive wire 731F, for example, to expand a retrieval basket. Spring 743F may serve to bias sheath 733F distally. As such, a user may enclose the distal end of drive wire 731F with minimal effort by allowing spring 743F to rotate control knob 603 distally and enclose the distal end of drive wire 731F, for example, to contract the retrieval basket.

It is understood that any of the aforementioned stroke lengths may be divided into two or more segments. For example, the end effector may be a Dakota basket. A first segment of the stroke length may open the end effector to a nominal size, and a second segment of the stroke length may open the end effector to a larger size for large stone release. Moreover, while the above discusses a proximal stroke limiter 739 abutting the neutral position of the drive wire 731 coupled to control knob 601, the disclosure is not so limited. In fact, a neutral position for drive wire 731 coupled to control knob 601 may be distal to a proximal stroke limiter 739. In this aspect, proximal stroke limiter 739 may ensure that drive wire 731 is retracted proximally away from a distal end of sheath 733. Moreover, one or springs may bias the distal movement, proximal movement, or both of drive wire 731 relative to sheath 733 by the one or more springs being positioned between block 735 and proximal stroke limiter 739, between block 735 and sheath extension 737, or between block 735 and a stop surface 738.

Figure 13:
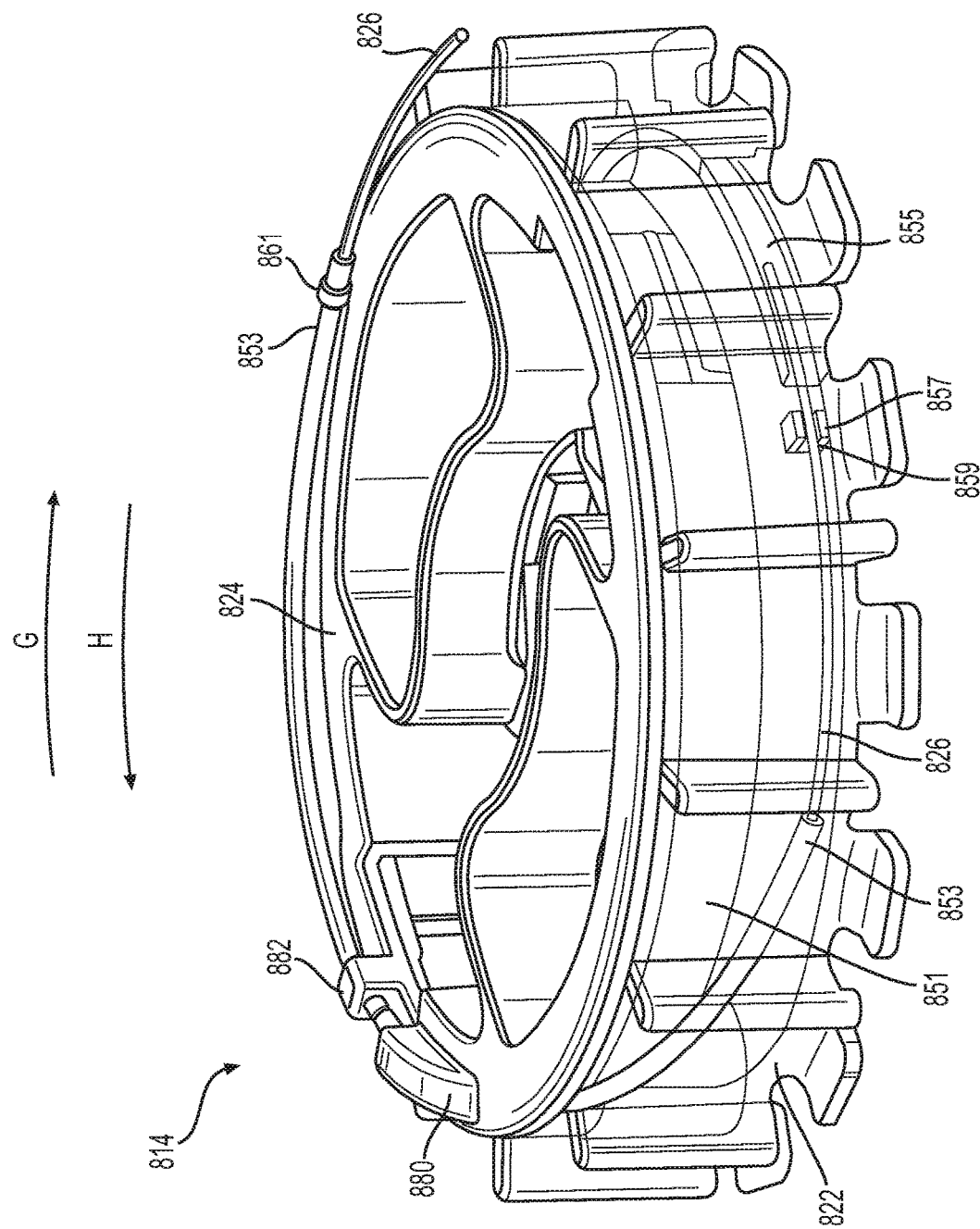
FIG. 13 illustrates a portion of an additional medical device, according to aspects of the present disclosure.

FIG. 13 illustrates another aspect of this disclosure with a partially see-through depiction of a medical device 814 which may allow a user to visually observe the extent to which a coiled element 826 is extended or retracted. Medical device 814 includes a handle 824 and a spool 822 that form a channel 851 that at least partially houses coiled element 826. Similar to FIG. 4A, handle 824 may include a guide ramp 880 and a tube support 882. Coiled element 826 may be partially surrounded by a tube 853. Spool 822 may include a tapered inner portion 855 into which a proximal end of coiled element 826 may be secured. Distal to tapered inner portion, spool 822 may also include an abutment surface 857 with a hole 859. Coiled element 826 may pass through hole 859. However, tube 853 may be sized to not fit through hole 859. Tube 853 may also include a radially thicker portion or a stop element 861 in a distal portion of tube 853.

It is noted that FIG. 13 illustrates medical device 814 with coiled element 826 fully dispensed. Tube 853 may have an inner diameter larger than coiled element 826, such that movement of coiled element 826 does not move tube 853 unless the proximal end of tube 853 is acted on by abutment surface 857 as spool 822 is rotated in direction G. The proximal portion of coiled element 826 may guide or direct the proximal portion of tube 853 toward abutment surface 857. Rotation of spool 822 in direction G may cause abutment surface 857 to abut and act on the proximal end of tube 853 to push tube 853 distally out of guide ramp 880. As such, the extension of tube 853 distally from guide ramp 880 may help to indicate to the user that coiled element 826 is almost fully dispensed. Such indication may help prevent the user from over-dispensing coiled element 826, disconnecting coiled element 826 from the internal connections within spool 822, and/or breaking coiled element 826.

Tube 853 may also help prevent the overwinding of coiled element 826 and/or help prevent coiled element 826 from becoming dislodged from guide 880, for example, to ensure that coiled element 826 may be dispensed again from medical device 814. Moreover, tube 853 may be clear or at least partially transparent such that a user may view the movement of coiled element 826 within tube 853. In one aspect, as the user winds spool 822 in direction H, coiled element 826 is retracted proximally because coiled element 826 is coupled to tapered portion 855. As coiled element 826 continues proximally, the user may visually observe the distal end of coiled element 826 enter tube 853, indicating to the user to stop winding spool 822 in order to prevent coiled element 826 from being further retracted and ensure that coiled element 826 remains within tube 853. With coiled element 826 within tube 853, the inner lumen of tube 853 may help to guide or direct coiled element 826 back through guide 880 when dispensing coiled element 826 again. Therefore, tube 853 may help to protect and dispense coiled element 826 again. Tube 853 may also include indications to provide information to the user regarding the extent to which coiled element 826 is retracted relative to a fully wound position. Additionally, stop element 861 may abut tube support 882 and prevent overwinding of coiled element regardless of whether the user is monitoring the winding position of coiled element 826.

It is noted that the spring configurations discussed above with respect to FIGS. 12A-12F may also be incorporated in medical device 814. For instance, medical device 814 may also include an end effector assembly having a drive wire and a sheath positioned radially within tube 853. As such, a user may compress medical device 814 and rotate a control knob to extend, retract, or otherwise position an end effector coupled to the drive wire relative to the sheath. Alternatively or additionally, medical device 814 may include springs between tube 853 and abutment surface 857. Moreover abutment surface 857 may be slideably coupled to spool 822, such that the user may adjust the position of abutment surface 857, thus adjusting the relative positions of tube 853 and a proximal end of coiled element 826 in tapered portion 855.

It is further noted that any of the aforementioned medical device may be used in conjunction with the insertion devices and adaptors discussed above. As such, a user may fixedly couple a medical device to an insertion device. Then, using one hand, the user may position or deflect the distal end of the delivery shaft by maneuvering the deflection lever, as well as extend or retract the coiled element by rotating the medical device coupled to the adaptor. The user may couple and control more than one medical device coupled to the insertion device, and thus may carry out different aspects of the medical procedure without repositioning the insertion device. The user may also use his or her other hand to perform other aspects of the procedure.

The systems, devices, and methods discussed herein may help to allow a user to dispense and/or retract a coiled element, such as a guidewire, optical fiber, catheter, filament, cable, or another shaft-like medical element while also controlling the position of a delivery shaft of an insertion device. The user may dispense only a length of the coiled element necessary for the procedure. The user may also retract the coiled element for use again during the medical procedure. Therefore, the length of the coiled element is adjustable throughout the procedure. Furthermore, the user may use one hand to extend and retract an end effector relative to a sheath, while also deflecting the distal end of the delivery shaft. Lastly, the devices and methods disclosed herein may help to reduce the number of medical professionals and the duration of the medical procedure.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. A medical system comprising:
   an insertion device including an insertion device handle having a proximal portion and a distal portion and a delivery shaft extending from the distal portion;
   a medical device including a spool, a medical device handle with a central opening, and a control knob movable relative to the spool and including at least one slot, wherein the spool and the medical device handle are rotatably movable to one another and form a channel, wherein the spool includes a plurality of spool teeth positioned on the spool facing the medical device handle, and wherein the medical device handle includes a plurality of handle teeth positioned on the medical device handle facing the spool; and
   an adaptor coupleable to a portion of the insertion device handle, wherein the adaptor includes a post element to be received within the central opening of the medical device handle.

2. The medical system of claim 1, wherein the medical device includes a coiled element at least partially positioned in the channel between the spool and the medical device handle, and wherein relative rotation of the spool and the medical device handle extends or retracts the coiled element.

3. The medical system of claim 2, wherein the coiled element includes an end effector, and wherein the coiled element is at least partially surrounded by a tube or sheath.

4. The medical system of claim 3, wherein the spool includes a lock element to secure a proximal end of the coiled element, and wherein the medical device handle includes a guide element to guide the coiled element and the tube or sheath from exterior to within the channel.

5. The medical system of claim 2, wherein the coiled element is partially surrounded by a tube, and wherein the tube includes a stop element at a distal end of the tube.

6. The medical system of claim 1, wherein the central opening and the post element are octagonal.

7. The medical system of claim 1, wherein the insertion device includes at least one port, and wherein the at least one port includes a seal.

8. The medical system of claim 2, wherein a proximal end of the coiled element extends proximal to the medical device to be coupled to an additional medical device.

9. The medical system of claim 1, wherein the insertion device includes a deflection lever positioned on the proximal portion of the insertion device handle on an opposite side of the insertion device handle from the adaptor; and
   wherein the system is configured for one handed use, the deflection lever is configured to be operated by a user's thumb, and the medical device is configured to be operated by a user's forefinger.

10. The medical system of claim 1, wherein the post element includes a plurality of projections separated by slots, and
    wherein the medical system further comprises a second medical device stacked on the adaptor.

11. The medical system of claim 2, wherein the spool includes a crank with a throughhole, and wherein the crank further includes a locking slot configured to lock the position of a proximal end of the coiled element.

12. The medical system of claim 1,
    wherein the medical device is configured to receive a wave spring is between the spool teeth and the handle teeth.

13. A medical device comprising:
    a rotatable spool element including a plurality of spool teeth;
    a handle element including a plurality of handle teeth, wherein the handle element is circular;
    a rotatable control knob movable relative to the spool element; and
    a coiled element including a sheath surrounding at least a portion of a drive wire, wherein a distal end of the drive wire is coupled to an end effector,
    wherein the spool element or the handle element form a channel to house at least a portion of the coiled element,
    wherein the plurality of spool teeth are positioned in a circle on the spool element facing the handle element,
    wherein the plurality of handle teeth are positioned in a circle on a circumference of the handle element facing the spool element, and
    wherein the medical device is configured to receive a biasing member between the spool teeth and the handle teeth.

14. The medical device of claim 13, wherein rotation of the spool element relative to the handle element extends or retracts the coiled element from the channel.

15. The medical device of claim 13, wherein compression of the medical device in a direction perpendicular to a plane of rotation of the spool member causes at least a portion of the spool teeth to engage with at least a portion of the handle teeth.

16. The medical device of claim 15, wherein, when the medical device is compressed, rotation of the control knob relative to the spool element extends or retracts the end effector from within the sheath.

17. A method of operating a medical system, comprising:
inserting an insertion device into a patient, wherein the insertion device includes a delivery shaft, a deflection mechanism, and at least one port;
coupling a medical device to the insertion device via an adaptor, wherein the medical device includes at least a spool, a handle, a control knob movable relative to the spool, and a coiled element at least partially stored between or within the spool and the handle, wherein the spool includes a plurality of spool teeth positioned on the spool facing the handle, wherein the handle includes a plurality of handle teeth positioned on the handle facing the spool, and wherein coupling the medical device via the adaptor rotatably locks the handle in place;
delivering the coiled element through the at least one port by rotating the spool.

18. The method of claim 17, further including contemporaneously deflecting a distal end of the delivery shaft by acting on the deflection mechanism and further delivering the coiled element by rotating the spool.

19. The method of claim 17, wherein the coiled element includes an end effector coupled to a drive wire and a sheath at least partially surrounding the drive wire, and
wherein the method further includes extending the end effector distally beyond the sheath by pressing the medical device toward the insertion device and rotating the control knob relative to the spool.

* * * * *